(12) United States Patent
Pines et al.

(10) Patent No.: US 6,420,371 B1
(45) Date of Patent: Jul. 16, 2002

(54) QUINAZOLINONE-CONTAINING PHARMACEUTICAL COMPOSITIONS FOR PREVENTION OF NEOVASCULARIZATION AND FOR TREATING MALIGNANCIES

(75) Inventors: Mark Pines, Rehovot; Israel Vlodavsky, Mevaseret Zion; Arnon Nagler, Jerusalem, all of (IL)

(73) Assignees: Madasit Medical Research Services & Development Co., Ltd., Jerusalem; Agricultural Research Organization-Ministry of Agricultural, Bet Dagan, both of (IL)

( * ) Notice: Subject to any disclaimer, the term of this patent is extended or adjusted under 35 U.S.C. 154(b) by 0 days.

(21) Appl. No.: 09/479,660

(22) Filed: Jan. 10, 2000

Related U.S. Application Data

(62) Division of application No. 08/797,703, filed on Feb. 11, 1997, now Pat. No. 6,028,075.

(51) Int. Cl.⁷ ............................................ A61K 31/505
(52) U.S. Cl. ....................................................... 514/259
(58) Field of Search ........................................ 514/259

(56) References Cited

U.S. PATENT DOCUMENTS

| | | | |
|---|---|---|---|
| 3,320,124 A | | 5/1967 | Waletzky et al. |
| 4,340,596 A | * | 7/1982 | Schein .................... 514/259 |
| 5,449,678 A | * | 9/1995 | Pines et al. ............. 514/259 |
| 6,028,075 A | * | 2/2000 | Pines et al. ............. 514/259 |

FOREIGN PATENT DOCUMENTS

| WO | WO 96/06616 | 3/1996 |
|---|---|---|

OTHER PUBLICATIONS

Adams et al., *Amer. J. Opthal.*, 118: 445–450 (1994).
Benezra et al., *Cancer Res.*, 52: 5656–5662 (1992).
Bischoff, *Trends Cell Biol.*, 5: 69–74 (1995).
Brooks et al., *Cell*, 79: 1157–1164 (1994).
Casas et al., *Ann. Rhem. Dis.*, 46: 763 (1987).
Castle et al., *J. Clin. Invest.* 87: 1883–1888 (1991).
Choi et al., *Arch. Surg.* 130: 257–261 (1995).
Cunliffe et al., *J. Med. Chem.*, 35: 2652 (1992).
Ferenczy et al., *Cancer*, 28: 1004–1018 (1971).
Folkman, *J. Natl. Cancer Inst.*, 82: 4–6 (1989).
Folkman, *Nature Medicine*, 1: 27–31 (1995).
Folkman, *Perspective in Biology and Medicine*, 29: 1–39 (1985).
Folkman and Klagsbrun, *Science*, 235: 442–447 (1987).
Folkman and Shing, *J. Biol. Chem.*, 267: 10931–10934 (1992).
Gospodarowicz et al., *Exp. Eye Res.*, 25: 75–89 (1977).
Gospodarowicz et al., *P.N.A.S. USA*, 73: 4120–4124 (1979).
Ingber et al., *Nature*, 348: 555–557 (1990).
Iruela–Arispe et al., *Lab Invest.*, 64: 174–186 (1991).
Jackson and Jenkins, *Exp. Cell Res.*, 192:v319–323 (1991).
Karvonen et al., *J. Biol. Chem.*, 265: 8415–8419 (1990).
Kershenobich et al., *N. Eng. J. Med.*, 318: 1709–1713 (1988).
Kivirikko, *Annals of Medicine*, 25: 113–126 (1993).
Mangrulker et al., *Biology of Reproduction*, 53: 636–646 (1995).
Miller et al., *J. Pathol.*, 145: 574–584 (1994).
Monesano et al., *J. Cell Biol.*, 97: 1648–1652 (1983).
Nickoloff et al., *Amer. J. Pathol.*, 44: 820–828 (1994).
Nicosia and Ottinetti, *Lab. Invest.*, 63: 115–122 (1990).
O'Reilly et al., *Cell*, 79: 316–328 (1994).
Peacock et al., *J. Exp. Med.*, 175: 1135–1138 (1992).
Salo et al., *J. Oral Pathol. Med.*, 19: 404 (1990).
Takahashi et al., *J. Clin. Invest.*, 93: 2357–2364 (1994).
Vlodavsky et al., *Basement Membranes: Cellular and Molecular Aspects*, D.H. Rohrbach and R. Timpl, Eds., Academic Press, Inc., Orlando, Florida, U.S.A., pp. 327–343 (1993).
Vlodavsky et al., *Cancer Res.*, 43: 2704–2711 (1983).
Vlodavsky et al., *P.N.A.S. USA* 84: 2292–2296 (1987).
Weidner et al., *Amer. J. Pathol.*, 143: 401–409 (1993).
Weidner et al., *N. Eng. J. Med.*, 324:1–8 (1991).
Zhang et al., *Endocrinology*, 134: 1089–1094 (1994).

\* cited by examiner

*Primary Examiner*—Jerome D. Goldberg
(74) *Attorney, Agent, or Firm*—Webb & Associates

(57) ABSTRACT

The invention provides a composition for attenuating neovascularization and treating malignancies, including a pharmaceutically effective amount of a compound having a formula:

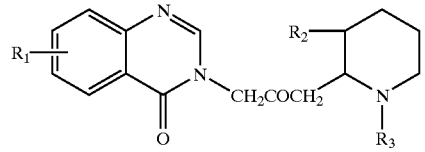

wherein:

$R_1$ is a number of the group consisting of hydrogen, halogen, nitro, benzo, lower alkyl, phenyl and lower alkoxy, $R_2$ is a member of the group consisting of hydroxy, acetoxy, and lower alkoxy, and $R_3$ is a member of the group consisting of hydrogen and lower alkenoxy carbonyl, as active ingredient therein, in combination with a pharmaceutically acceptable carrier.

3 Claims, 20 Drawing Sheets

QUINAZOLINONE-CONTAINING PHARMACEUTICAL COMPOSITIONS FOR PREVENTION OF NEOVASCULARIZATION AND FOR TREATING MALIGNANCIES

This is a Divisional application of U.S. patent application No. 08/797,703, filed on Feb. 11, 1997, now U.S. Pat. No. 6,028,075.

FIELD AND BACKGROUND OF THE INVENTION

The present invention relates to compositions containing quniazolinones. More particularly, the present invention relates to a composition, containing a quinazolinone derivative, useful for the treatment of angiogenic-associated diseases, as well as for the treatment of malignancies, including inhibition of primary tumor growth, tumor progression and metastasis.

Malignancies are characterized by the growth and spread of tumors. A number of factors are important in the progression of this disease. One crucial factor is angiogenesis, a complex process in which capillary blood vessels grow in an ordered sequence of events [J. Folkman and M. Klagsbrun, Science, Vol. 235, pp 442–447 (1987); J. Folkman and Y. Shing, J. Biol. Chem., Vol. 267, pp. 19031–10934 (1992)]. Once a tumor has started, every increase in tumor cell population must be preceded by an increase in new capillarities that converge on the tumor and supply the cells with oxygen and nutrients [J. Folkman, Perspect, in Biol, and Med., Vol 29, p. 10–36 (1985); J. Folkman, J. Natl. Cancer Inst. Vol. 82, pp. 4–6 (1989); M. Weidner, et al., Amer. J. Pathol. Vol. 143, pp. 401–409 (1993)]. Tumors may thus remain harmless and confined to their tissue of origin, as long as an accompanying angiogenic program is prevented from being activated. Since the angiogenesis-dependent step in tumor progression is shared by solid tumors of all edologies, the ability to inhibit tumor-associated angiogenesis is a most promising approach in combating cancer [M. S. O'Reilly, et al., Cell. Vol. 79, pp. 316–328 (1994)].

A substantial body of experimental evidence supports the hypothesis that tumor angiogenesis is fundamental for the growth and metastasis of solid tumors [J. Folkman,ibid. (1989); N. Weidner, et al., ibid, (1993); M. S. O'Reilly, et al., ibid. (1994); N. Weidner, et al., N. Eng. J. Med., Vol. 324, pp. 1–8 (1991)]. Indeed, the majority of solid tumors are not even clinically detectable until after the occurrence of neovascularizartion, whose induction in solid tumors is mediated by one or more angiogenic factors [J. Folkman, ibid. (1987); J. Folkman and Y. Shin, ibid, (1992)].

Furthermore, angiogenesis is also important in a number of other pathological processes, including arthritis, psoriasis, diabetic retinopath, chronic inflammation, scleroderma, hemangioma, retrolental fibroplasia and abnormal capillary proliferation in homophiliac joints, prolonged menstruation and bleeding, and other disorders of the female reproductive system [J. Folkman, Nature Medicine, Vol. 1, pp. 27–31, (1995); J. W. Miller, et al., J. Pathol, Vol. 145, pp. 574–584 (1994), A. P. Adamid, et al., Amer J. Ophthal., Vol. 118, pp. 445–450 (1994), K. Takahashi, et al., J. Clin. Invest., Vol. 93, pp. 2357–2364 (1994); D. J. Peacock, et al., J. Exp. Med., Vol. 175, pp. 1135–1138 (1992); B. J. Nickoloff, et al., Amer. J. Pathol., Vol. 44, pp. 820–828 (1994); J. Folkman, Steroid Hormones and Uterine Bleeding, N. J. Alexander and C. d'Arcangues, Eds., American Association for the Advancement of Science Press, Washington, D.C. U.S.A., pp. 144–158 (1992)].

Thus, clearly methods of blocking the mechanism of angiogenesis are necessary. The basic mechanism of angiogenesis is as follows. Briefly, when a new capillary sprout grows from the side of the venule, endothelial cells degrade basement membrane, migrate inward an angiogenic source, proliferate, form a lumen, join the tips of two sprouts to generate a capillary loop, and manufacture new basement membrane [J. Folkman., Perspective in Biology and Medicine, Vol. 29, pp. 1–36 (1985)].

Degradation and remodeling of the ECM are essential processes for the mechanism of angiogenesis. In addition, ECM components synthesized by endothelial cells (i.e. collagens, laminin, thrombospondin, fibronectin and SPARC) function to regulate endothelial cell growth, migration and shape [J. Bischoff, Trends Cell Biol., No. 5, pp. 69–74 (1995)]. Bovine aortic endothelial cells (BAE) undergoing sprouting and tube formation synthesize type I collagen and SPARC. It was proposed that type I collagen may be involved in directing migration and assembly of the BASE cells [M. L. Iruela-Arispe, et al., Lab. Invest, No. 64, pp. 174–186 (1991). It was also found that exogenous type I collagen promoted rapid tube formation by confluent human dermal microvascular endothelial cells [C. J. Jackson and K. L. Jenkins, Exp. Cell. Res., No. 192, pp. 319–323 (1991)]. the tubes contained collagen fibrils in the luminal spaces, suggesting that the endothelial cells use the fibrils to fold and align into tube structures.

Furthermore, in order to extend a capillary blood vessel, interactions must occur between ECM components and the surrounding matrix molecules, which provide a scaffold for the ECM components of the new vessel [Brooks, P. C. et al., Cell, Vol. 79, p. 1157–1164, (1994)]. Disruption of cell-matrix interactions induced apoptosis in human endothelial cells. It has been demonstrated that integrin $\alpha_2\beta_3$, which has an enhanced expression in angiogenic vascular cells, promotes a survival signal, since inhibitors of this integrin cause unscheduled apoptosis and disintegration of newly formed blood vessels.

In order to treat angiogenesis-related diseases, several inhibitors of the above mechanism of angiogenesis are being studied, including platelet factor 4, the fumagillin derivative AGM 1470, Interferon $\alpha_2$a, thrombospondin, angiostatic steroids, and angiostatin [J. Folkman, ibid, (1995); M. S. O'Reilly, et al., ibid, (1994); V. Castle, et al., J. Clin. Invest., Vol. 87, pp. 1883–1888; D. Ingber, et al., Nature, Vol. 348, pp. 555–557]. All of these compounds have disadvantages. For example, endostatin and angiostatin are proteins, so that they have all of the disadvantages of proteins, including the requirement for being administered parenterally. Therefore, a non-protein inhibitor which would selectively block the underlying mechanism of angiogenesis without adversely affecting other physiological functions, and which could be administered by many different routes, would be extremely useful.

In addition, many of the compounds that are now being evaluated as antiangiogenic agents are proteins, e.g., antibodies, thrombospondin, angiostatin, platelet factor IV [J. Folkman, ibid, (1995); M. S. O'Reilly, et al., ibid, (1994); V. Castle, et al., ibid., P. C. Brooks, et al., ibid. (1994)], which suffer from poor bioavailability and are readily degraded in the body. Hence, these substances should be administered in high doses and frequencies.

Other approaches for cancer treatment focus on cytotoxic therapies, such as chemotherapy or radiation treatments, in order to kill actively proliferating cells. Unfortunately, these therapies are highly toxic to non-cancer cells and cause severe side effects, such as bone marrow suppression, hair loss and gastrointestinal disturbances.

As noted above, degradation and remodeling of the ECM are essential processes for the mechanisms of angiogenesis. Such processes involve the synthesis of a number of components of the ECM, such as collagen. The synthesis of collagen is also involved in a number of other pathological condition. For example, clinical conditions and disorders associated with primary or secondary fibrosis, such as systemic sclerosis, graft-versus-host disease (GVHD), pulmonary and hepatic fibrosis and a large variety of autoimmune disorders are distinguished by excessive production of connective tissue, which results in the destruction of normal tissue architecture and function. These diseases can best be interpreted in terms of perturbations in cellular functions, a major manifestation of which is excessive collagen synthesis and deposition. The crucial role of collagen in fibrosis has prompted attempts to develop drugs that inhibit its accumulation [K. I. Kivirikko, *Annals of Medicine*, Vol. 25, pp. 113–126 (1993)].

Such drugs can act by modulating the synthesis of the procollagen polypeptide claims, or by inhibiting specific post-translation events, which will lead either to reduced formation of extra-cellular collagen fibers or in an accumulation of fibers with altered properties. Unfortunately, only a few inhibitors of collagen synthesis are available, despite the importance of this protein in sustaining tissue integrity and its involvement in various disorders.

For example, cytotoxic drugs have been used in an attempt to slow the proliferation of collagen-producing fibroblasts [J. A. Cases, et al., *Ann. Rhem. Dis.*, Vol. 46, p. 763 (1987)], such as colchicine, which slows collagen secretion into the extracellular matrix [D. Kershenobich, et al., *N. Engl. J. Med.*, Vol 318, p. 1709 (1988)], as well as inibitors of key collagen metabolism enzymes [K. Karvonen, et al., *J. Biol. Chem.*, Vol. 265, p. 8414 (1990); C. J. Cunliffe, et al., *J. Med. Chem.*, Vol. 35, p. 2652 (1992)].

Unfortunately, none of these inhibitors are collagen-type specific. Also, there are serious concerns about the toxic consequences of interfering with biosynthesis of other vital collagenous molecules, such as Clq in the classical complement pathway, acetylcholine esterase of the neuro-muscular junction endplate, conglutinin and pulmonary surfactant apoprotein.

Other drugs which can inhibit collagen synthesis, such as nifedipine and phenytoin, inhibit synthesis of other proteins as well, thereby non-specifically blocking the collagen biosynthesis pathway [T. Salo, et al., *J. Oral Pathol, Med.*, Vol. 19, p. 404 (1990)].

Collagen cross-linking inhibitors, such as β-aminopropionitrile, are also non-specific, although they can serve as useful anti-fibrotic agents. Their prolonged use causes lathritic syndrome and interferes with elastogenesis, since elastin, another fibrous connective tissue protein, is also cross-linked. In addition, the collagen cross-linking inhibitory effect is secondary, and collagen overproduction has to precede its degradation by collagenase. Thus, a type-specific inhibitor of the synthesis of collagen itself is clearly required as an anti-fibrotic agent.

Such a type-specific collagen synthesis inhibitor is disclosed in U.S. patent application Ser. No. 08/181,066 for the treatment of a fibrotic condition, restenosis or glomerulosclerosis. This specific inhibitor is a composition with a pharmaceutically effective amount of a pharmaceutically active compound of a formula:

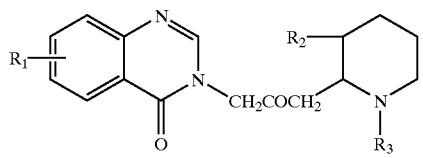

wherein:
- $R_1$ is a member of the group consisting of hydrogen, halogen, nitro, benzo, lower, alkyl, phenyl and lower alkoxy;
- $R_2$ is a member of the group consisting of hydroxy, acetoxy and lower alkoxy, and
- $R_3$ is a member of the group consisting of hydrogen and lower alkenoxy-carbonyl. Of this group of compounds, Halofuginone has been found to be particularly effective for such treatment.

U.S. Pat. No. 5,449,678 discloses that these compounds are effective in the treatment of fibrotic conditions such as sclerodenna and GVHD. WO No. 96/06616 further discloses that these compounds are effective in treating restenosis. The two former conditions are associated with excessive collagen deposition, which can be inhibited by Halofuginone. Restenosis is characterized by smooth muscle cell proliferation and extracellular matrix accumulation within the lumen of affected blood vessels in response to a vascular injury [Choi et al., *Arch. Surg.* Vol. 130, p. 257–261 (1995)]. One hallmark of such smooth muscle cell proliferation is a phenotypic aberation, from the normal contractile phenotype to a synthetic one. Type I collagen has been shown to support such a phenotypic alteration, which can be blooded by Halofuginone [Choi et al., *Arch. Surg.*, Vol. 130, p. 257–261 (1995); U.S. Pat. No. 5,449,678]. Thus, Halofuginone can prevent such differentiation of smooth muscle cells after vascular injury by blocking the synthesis of type I collagen. Other in vitro studies show that Halofuginone can also inhibit the proliferation of 3T3 fibroblast cells [U.S. Pat. No. 5,449,678].

However, the in vitro action of Halofuginone does not always predict its in vivo effects. For example, Halofuginone inhibits the synthesis of collagen type I in bone chrondrocytes in vitro, as demonstrated in U.S. Pat. No. 5,449,678. However, chickens treated with Halofuginone were not reported to have an increased rate of bone breakage, indicating that the effect is not seen in vivo. Thus, the exact behavior of Halofuginone in vivo cannot always be predicted from in vitro studies.

Furthermore, the ability of Halofuginone on other related quinolinones to block or inhibit physiological processes related to tumor growth and progression is not known in the prior art. Although Halofuginone has been shown to have a specific inhibitory effect on the synthesis of type I collagen, such inhibition has not been previously shown to slow or halt tumor progression, particularly in vivo.

There is thus a widely recognized unmet medical need for an inhibitor of tumor progression which is particularly effective in vivo, substantially without adversely affecting other physiological processes.

SUMMARY OF THE INVENTION

Unexpectedly, in has been found as described in the examples below, that Halofuginone can also slow or halt tumor progression in vivo, possibly by inhibiting angiogenesis, or by blocking ECM deposition, or possibly through both mechanisms, although another mechanism or mechanisms could also be responsible. While inhibition of angiogenesis and of ECM deposition, or a combination thereof, are proposed at plausible mechanisms, it is not desired to be limited to a single mechanism, not is it necessary since the in vivo data presented below clearly demonstrate the efficiency of Halofuginone as an inhibitor of tumor progression in vivo.

According to an embodiment of the present invention, there is provided a comparison for treating a tumor, including a pharmaceutically effective amount of a compound in combination with a pharmaceutically acceptable carrier, the compound being a member of a group having a formula:

[Chemical structure]

wherein:

$R_1$ is a member of the group consisting of hydrogen, halogen nitro, benzo, lower alkyl phenyl, and lower alkoxy;

$R_2$ is a member of the group consisting of hydroxy, acetoxy, and lower alkoxy, and $R_3$ is a member of the group consisting of hydrogen and lower alkenoxy.

According to another embodiment of the present invention, there is provided a method of manufacturing a medicament for treating a tumor, including the step of placing a pharmaceutically effective amounts of a compound in a pharmaceutically acceptable carrier, the compound being a member of a group having a formula:

[Chemical structure]

wherein:

$R_1$ is a member of the group consisting of hydrogen, halogen, nitro, benzo, lower alkyl, phenyl, and lower alkoxy;

$R_2$ is a member of the group consisting of hydroxy, acetoxy and lower alkoxy, and $R_3$ is a member of the group consisting of hydrogen and lower alkenoxy-carbonyl.

According to yet another embodiment of the present invention, there is provided a method of manufacturing a medicament for substantially inhibiting neovascularization, including the step of placing a pharmaceutically effective amount of a compound in a pharmaceutically acceptable carrier, the compound being a member of a group having a formula:

[Chemical structure]

wherein:

$R_1$ is a member of the group consisting of hydrogen, halogen, nitro, benzo, lower alkyl, phenyl, and lower alkoxy;

$R_2$ is a member of the group consisting of hydroxy, acetoxy, and lower alkoxy, and $R_3$ is a member of the group consisting of hydrogen and lower alkenoxy-carbonyl.

According to still another embodiment of the present invention, there is provided a method for the treatment of angiogenesis in a subject, including the step of administering a pharmaceutically effective amount of a compound having a formula:

[Chemical structure]

wherein:

$R_1$ is a member of the group consisting of hydrogen, halogen, nitro, benzo, lower alkyl, phenyl, and lower alkoxy;

$R_2$ is a member of the group consisting of hydroxy, acetoxy and lower alkoxy, and $R_3$ is a member of the group consisting of hydrogen and lower alkenoxy carbonyl.

According to still another embodiment of the present invention, there is provided a method for the treatment of a tumor in a subject, including the step of administering a pharmaceutically effective amount of a compound having a formula:

[Chemical structure]

wherein:

$R_1$ is a member of the group consisting of hydrogen, halogen, nitro, benzo, lower alkyl phenyl and lower alkoxy, $R_2$ is a member of the group consisting of hydroxy, acetoxy and lower alkoxy, and $R_3$ is a member of the group consisting of hydrogen and lower alkenoxy-carbonyl.

There is also provided a composition for inhibiting cell proliferation enabled by a deposition of an extracellular matrix, including a pharmaceutically effective amount of a compound having a formula:

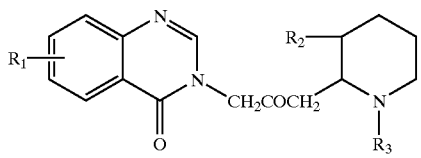

wherein:
  R₁ is a member of the group consisting of hydrogen, halogen, nitro, benzo, lower alkyl, phenyl and lower alkoxy;
  R₂ is a member of the group consisting of hydroxy acetoxy and lower alkoxy, and
  R₃ is a member of the group consisting of hydrogen and lower alkoxy-carbonyl.

Preferably, the specific compound in each of the above embodiments is Halofuginone.

While the invention will now be described in connection with certain preferred embodiments in the following figures and examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following figures and examples which include preferred embodiments will serve to illustrate the practice of this invention, it being understood that the particulars shown are by way of example and for purposes of illustrative discussion of preferred embodiments of the present invention only, and are presented in the cause of providing what is believed to be the most useful and readily understood description of formulation procedures as well as of the principles and conceptual aspects of the invention.

BRIEF DESCRIPTION OF THE DRAWINGS

The invention is herein described, by way of example only, with reference to the accompanying drawings, wherein.

DESCRIPTION OF PREFERRED EMBODIMENTS

Unexpectedly, in has been found, as described in the examples below, that Halofuginone can also slow or halt tumor progression in vivo, possibly by inhibiting angiogenesis or by substantially completely inhibiting deposition of ECM components, or a combination thereof, although another mechanism or mechanisms could also be responsible. Indeed, irrespective of the specific mechanism, the data presented below clearly demonstrate the efficacy of Halofuginone in vivo at inhibiting tumor progression.

Such a finding is unexpected for three reasons. First, the behavior of Halofuginone in vitro does not exactly correspond to its behavior in vivo. This can be demonstrated by the differential effect of Halofuginone observed will bone chondrocytes in vivo and vitro. Halofuginone inhibits the synthesis of collagen type I in chrondrocytes in vitro, as demonstrated in U.S. Pat. No. 5,449,678. However, chickens treated with Halofuginone were not reported to have an increased rate of bone breakage, indicating that the effect is not seen in vivo. Thus, the exact behavior of Halofuginone in vivo cannot always be predicted from in vitro studies.

Second, the only previously known examples of the inhibition of cell proliferation by Halofuginone involved either smooth muscle cells which had become phenotypically altered in response in a vascular injury, or 3T3 fibroblasts [WO No. 96/06616 and Choi et al., *Arch Surg.*, Vol. 130, p. 257–261 (1995)]. These cells simply proliferated without organization. By contrast, angiogenesis involves the formation of highly organized vascular structures. Thus, the finding that Halofuginone can inhibit such angiogenesis is both novel and non-obvious.

Furthermore, the examples given below clearly demonstrate that Halofuginone is also effective in the inhibition of cell proliferation enabled by the deposition of an extracellular matrix, in vivo as well as in vitro. Such specific inhibition has never been demonstrated before, particularly in vivo.

Thus, nothing in the prior art taught or suggested that Halofuginone would be useful in the treatment of malignancies in vivo. Furthermore, the ability of Halofuginone, and related compounds, to slow or halt tumor progression, and to inhibit cell proliferation enabled by the deposition of an extracellular matrix, at both novel and non-obvious. The demonstration of such an ability in vivo is particularly unexpected, given the differential responses seen in vitro and in vivo to Halofuginone. The present invention may be more readily understood with reference to the following illustrative examples and figures. It should be noted than although reference is made exclusively to Halofuginone, it is believed that the other quinazolinone derivatives described and claimed in U.S. Pat. No. 3,320,124, the teachings of which are incorporated herein by reference, have similarly properties.

EXAMPLE 1

Inhibition of in vivo Tumor Growth in Mice by Halofuginone

Figure 1A:
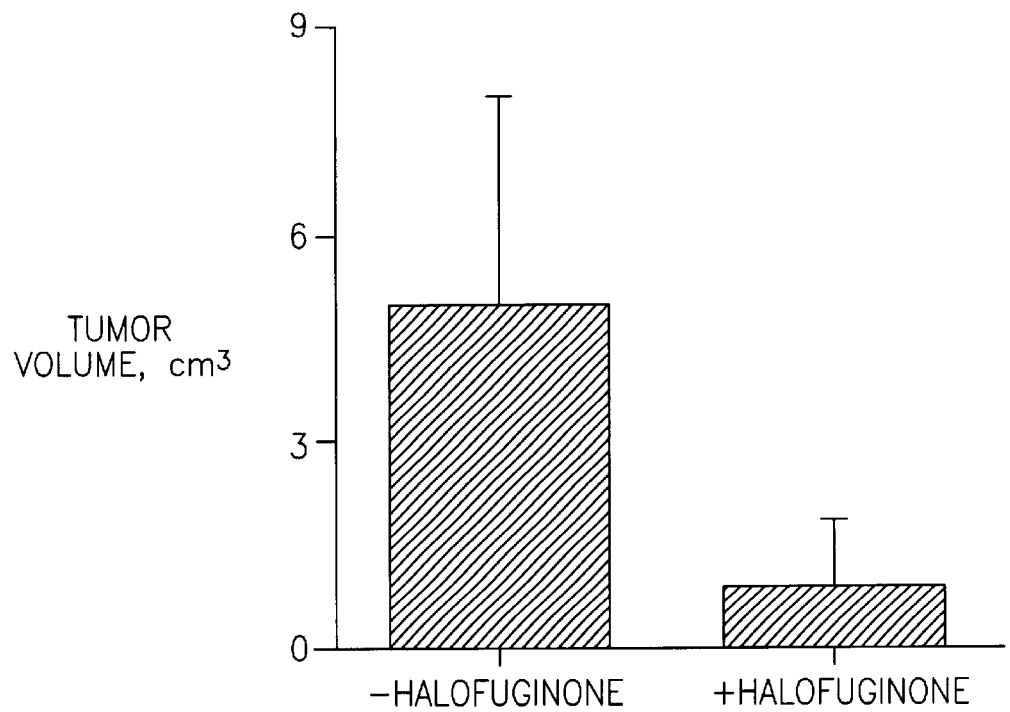
FIGS. 1A–1F illustrate the inhibition and apoptosis of in vivo tumor growth in mice by Halofuginone.
Figure 1B:
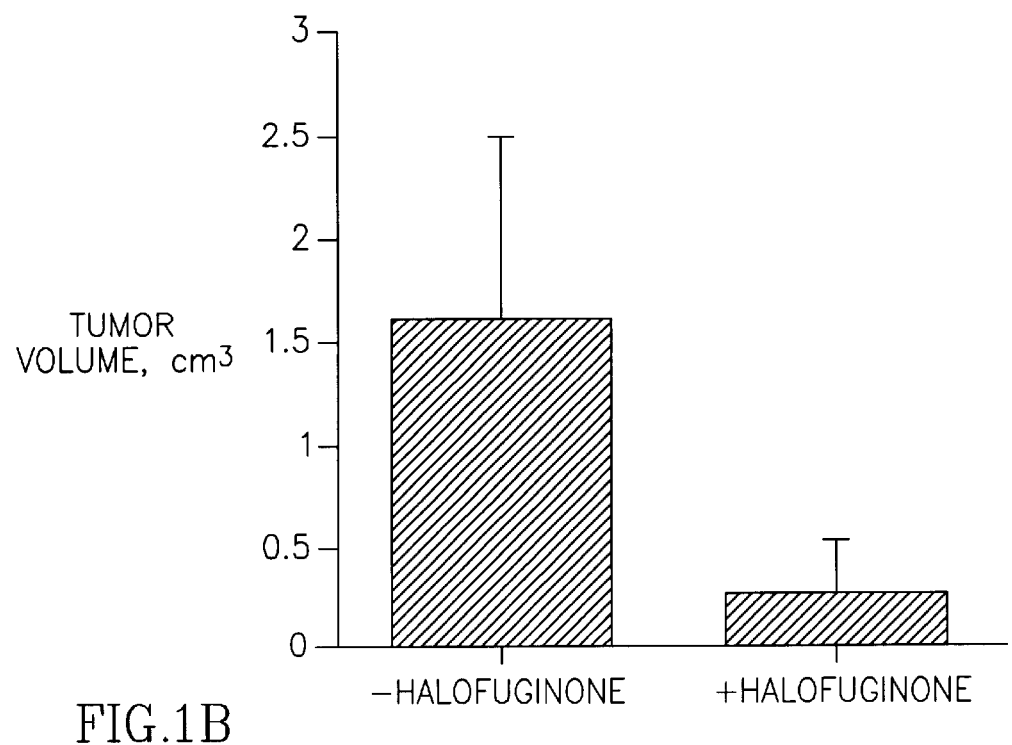
Figure 1C:
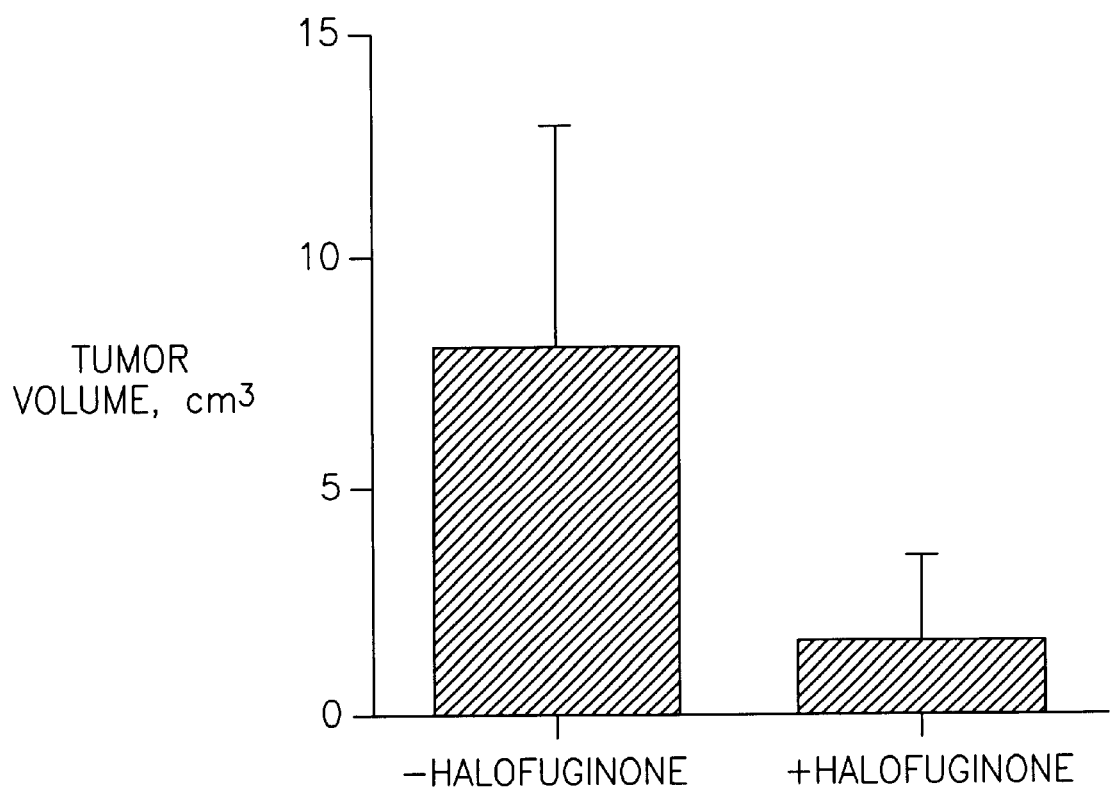
Figure 1D:
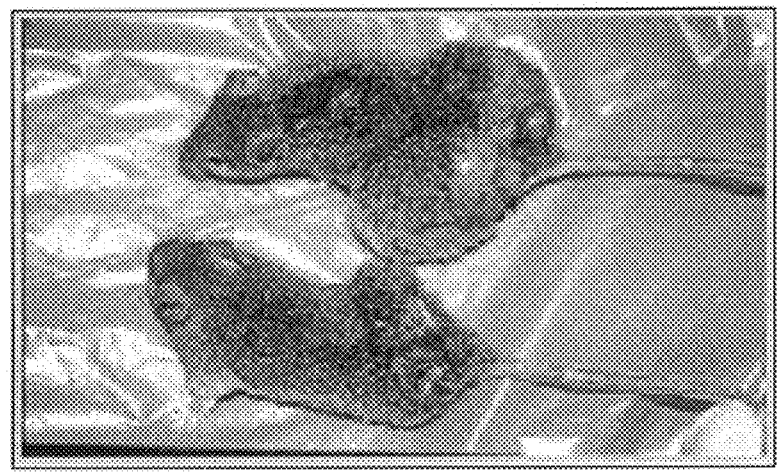
Figure 1E:
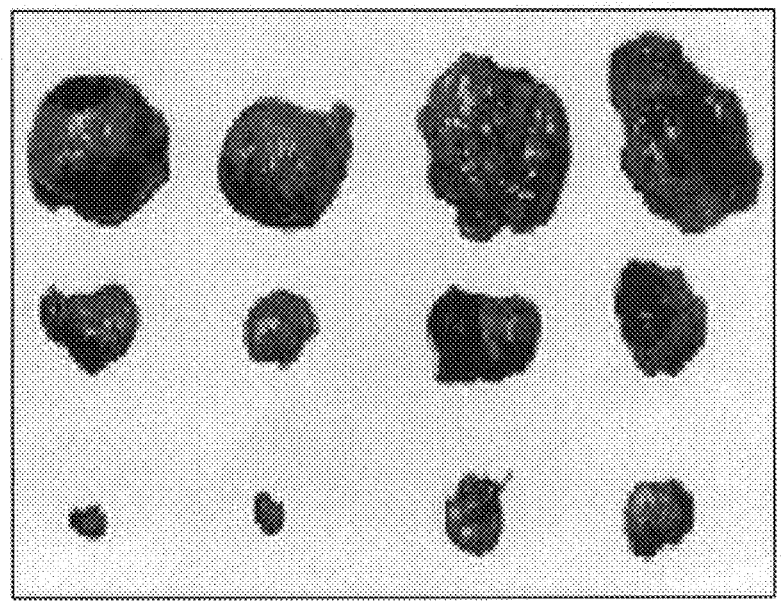

The inhibition of growth of two different tumors was examined in vivo in mice. The first type of tumor was T50 bladder carcinoma in C3H mice, and the second type was EHS sarcoma in C57BL/6 mice. Unexpectedly, Halofuginone was shown to have a significant inhibitory effect on tumor growth and progression in these in vivo models. Quantitative results are shown in FIGS. 1A, 1B and 1C. A photograph of control and halofuginone treated mice is presented in FIG. 1D. Photographs of the tumors excised from control mice and mice fed with halofuginone containing diet (5 and 10 mg/kg food) are presented in FIG. 1E. Histological sections of the tumors are presented in FIG. 1F.

C3H mice were divided into two groups (6 mice each). The experimental group received a diet containing 5 mg/kg of Halofuginone 3 days prior to the injection of T50 bladder carcinoma cells and during 2 weeks after. Cultured T50 cells, a more aggressive variant of the chemically induced MBT2 mouse bladder carcinoma, were dissociated with trypsin/EDTA into a single cell suspension ($10^6$ cells/ml) in growth medium and inoculated s.c. in two sites on the dorsa of mice. The right side received $0.4 * 10^5$ cells, and the left side received $2 * 10^5$ cells. The tumor size was estimated by measurement of tumor length in two directions, using the formula $V=LW^2/2$, where V is volume, L is length and W is width. At the end of the experiment at day 17, the mice were weighed, the tumors were excised and a sample of the tumor tissue was fixed and processed for histological examination.

Tumor size in C3H mice which were fed with Halofuginone was significantly reduced, by about 70–80%, as compared to control mice maintained on a normal diet, as shown in FIG. 1A and 1B. The anti-tumor effect of Halofuginone was observed both at the high tumor cell dose, with a volume of $5.00\pm3.07$ cm$^3$ for control mice and $1.0\pm0.92$ cm$^3$ for Halofuginone containing diet, and the lower tumor cell dose, with a volume of $1.53\pm0.98$ cm$^3$ for Halofuginone containing diet, and the lower tumor cell dose, with a volume of $1.63\pm0.98$ cm$^3$ for control mice and $0.29\pm0.28$ cm$^3$ for Halofuginone fed mice. Furthermore, the overall weight of the Halofuginone treated C3H mice was lower than the weight of the untreated mice, $24\pm3.1$ g and $0\pm3.8$ g, respectively, due to the lower tumor burden. Data for all mice are shown in Table 1.

TABLE 1

Effect of Halofuginone on T50 Tumor Size (cm$^3$)

| Sample No. | −Halofuginone | | +Halofuginone | |
|---|---|---|---|---|
| | $0.4 * 10^5$ cells | $2 * 10^5$ cells | $0.4 * 10^5$ cells | $2 * 10^5$ cells |
| 1 | 2.6 | 4.3 | 0.036 | 0.7 |
| 2 | 2.7 | 10.1 | 0.064 | 0.1 |
| 3 | 0.4 | 6.1 | 0.150 | 1.1 |
| 4 | 1.0 | 6.6 | 0.730 | 2.0 |
| 5 | 0.9 | 0.7 | 0.510 | 1.1 |
| 6 | 2.2 | 2.2 | NA | NA |

Animals bearing Engelbreth-Holm-Swarm (EHS) tumors were sacrificed and the tumor tissue was excised and minced under aseptic conditions. The EHS tumor is characterized by a large amount of basement membrane components. A suspension of the tumor tissue in 0.2 ml of PBS was injected subcutaneously in the dorsal posterior region of C57BL/6 male mice. The mice were divided into two groups of 10 mice each. The animals of the experimental group were fed with a diet containing 5 mg/kg Halofuginone for 3 days prior to tumor injection and during 3 weeks after. The tumor size was estimated by measurement of tumor length in two directions, using the formula $V=LW^2/2$. On the final day of the experiment, i.e., 20 days after tumor injector, the mice were weighed the tumors were exceed and a sample of the tumor tissue was fixed and processed for histological examination.

Tumor size in C57BL/6 mice which were fed Halofuginone was reduced by about 75% as compared to control mice, with volumes of $1.72\pm1.85$ cm$^3$ and $8.15\pm4.88$ cm$^3$, respectively, as shown in FIG. 1C. The anti-tumor effect of Halofuginone was reflected by the nearly normal weight of Halofuginone-fed mice, $19.7\pm0.47$ g, as opposed to the approximately 1.6 fold higher weight of control mice, $33.3\pm2.49$ g. due to the tumor burden. Data for all mice are shown in Table 2.

TABLE 2

Effect of Halofuginone on EHS Tumor Size

| Sample No | −Halofuginone | +Halofuginone |
|---|---|---|
| 1 | 12.6 | 1.3 |
| 2 | 5.8 | 1.2 |
| 3 | 3.2 | 1.3 |
| 4 | 12.6 | 1.7 |
| 5 | 4.9 | 0 |
| 6 | 6.8 | 0 |
| 7 | 4.9 | 2.2 |
| 8 | 18.9 | 0.04 |
| 9 | 2.8 | 6.5 |
| 10 | 9.0 | 3.0 |

Figure 1F:
Figure 1F:
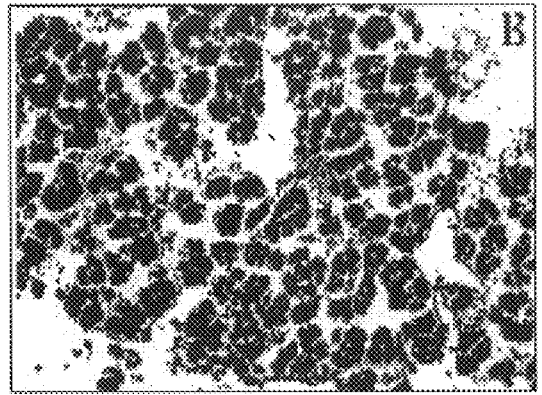
Figure 1F:
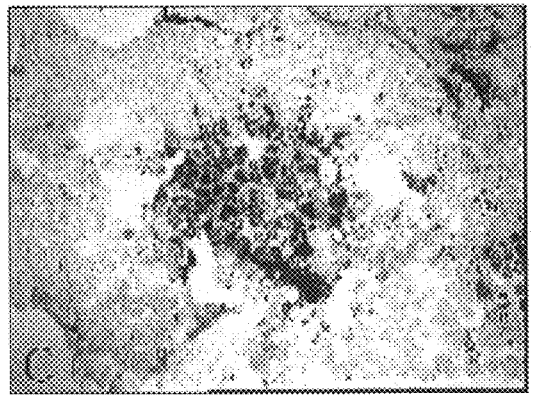
Figure 1F:
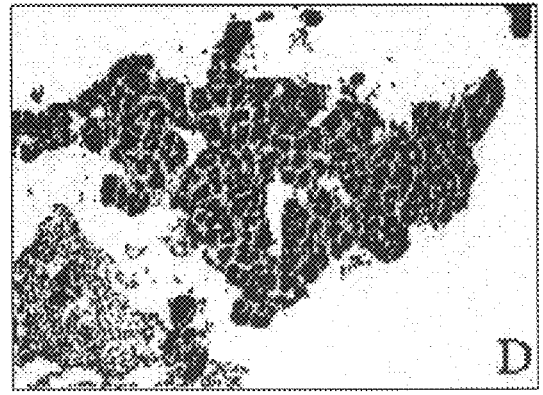

Histological sections of the tumors were subjected to tunnel staining [Gavrieli, Y. et al., *J. Cell Biol.*, Vol. 119, pp. 493–501, 1992], in order to evaluate the extent of tumor cell necrosis and apoptosis. As demonstrated in FIG. 1F panel B, the majority of cells in tumor sections derived from halofuginone treated mice exhibited an intense staining, as compared to only a small percentage of the cells the were stained in sections derived from tumors in untreated mice (FIG. 1F, panel A). The high degree of cell apoptosis and necrosis in halofuginone treated tumors is in all likelihood due to an inhibition of angiogenesis and DCM deposition, both critical factors supporting growth and survival of the tumor cells.

EXAMPLE 2

Halofuginone-induced inhibition of $^3$H-thymidine incorporation into vascular endothelial cells Cultures of vascular endothelial cells were established from bovine aorta as previously described [D. Gospodarowicz, et al., *Proc. Natl. Acad. Sci. U.S.A.*, Vol. 73, p. 4120 (1979)]. Bovine aortic endothelial cells were plated ($4\times10^4$ cells/16 mm well) in DMEM (1 g glucose/liter) supplemental with 10% calf serum, 50 U/ml penicillin, and 50 $\mu$/ml streptomycin at 37° C. in 10% $CO_2$ humidified incubators.

Four days after plating, the subconfluent cells were exposed to increasing concentrations of Halofuginone (100–500 ng/ml), in the absence of presence of 1 ng/ml bFGF. $^3$H-thymidine (1 $\mu$Ci/well) was then added for an additional 48 hours, and DNA synthesis was assayed by measuring the radioactivity incorporated into trichloroacetic acid insoluble material [M. Benezra, et al., Cancer Res., Vol 52, pp. 5656–5662 (1992); I. Vlodavsky, et al., Proc. Natl. Acad. Sci. U.S.A. Vol. 84, pp. 2292–2296 (1987)].

Figure 2A:
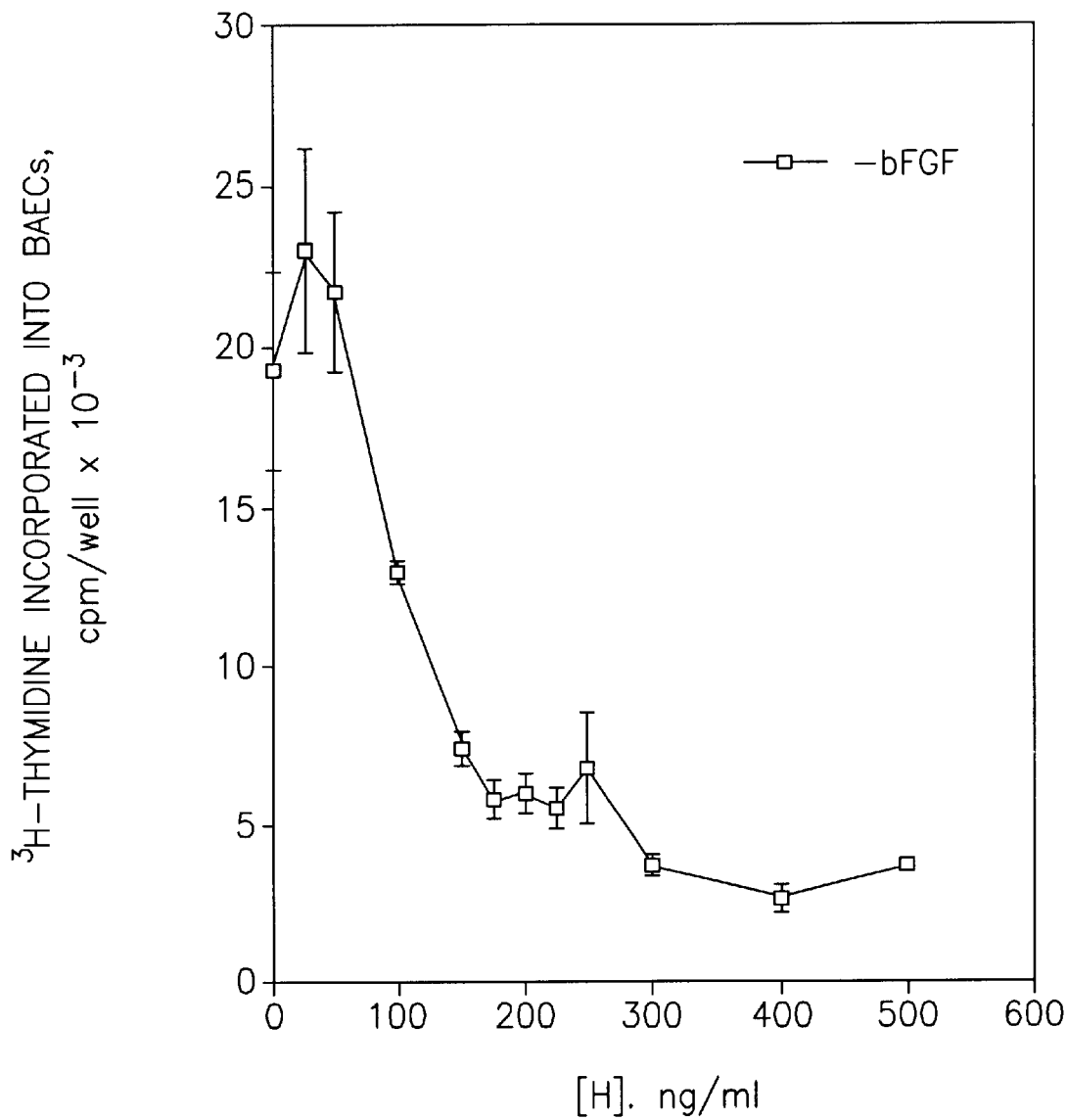
FIGS. 2A and 2B show the effect of Halofuginone on ³H-thymidine incorporation into bovine aortic endothelial cells maintained in culture, in the absence or the presence of bovine fibroblast growth factor (bGFG)
Figure 2B:
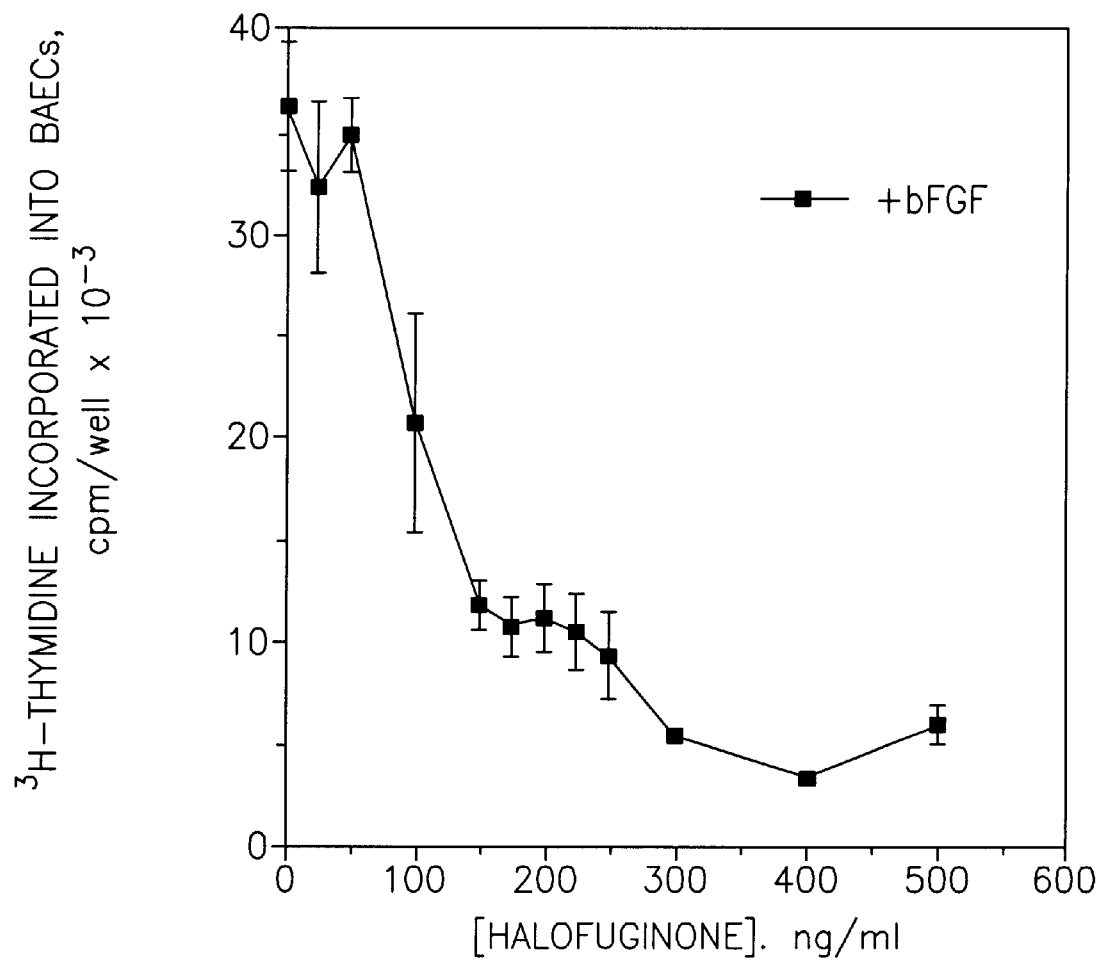

FIG. 2A shows the results obtained in the absence of bFGF, while FIG. 2B shows the results obtained in the presence of bFGF. As demonstrated in FIGS. 2A and 2B, 50% inhibition of $^3$H-thymidine incorporation was obtained at 100 ng/ml Halofuginone, regardless of whether or not bFGF (1 ng/ml) was added to the culture medium.

EXAMPLE 3

Organization of Endothelial Cells into Capillary-like Networks

Halofuginone was found to prevent the organization of endothelial cells into a defined structure, and specifically inhibited the organization of these cells into capillary-like networks. Results are shown in FIGS. 3A and 3B.

Type I collagen was prepared from the tail tendons of adult Sprague Dawley rats. Briefly, the collagen fibers were solubilized by a slow stirring for 48 h at 4° C. in a sterile, 1/1000 (w/v) acetic acid solution (300 ml for 1 g of collagen). The resulting solution was filtered through a sterile triple gauze and centrifuged at 16,000 g for 1 h at 4° C. The supernatant was then extensively dialyzed against 1/10. DMEM and stored at 4° C. The collagen matrix gel was obtained by simultaneously raising the pH and ionic strength of the collagen solution. For this purpose, 7 vol of collagen solution were quickly mixed with 1 vol of 10X Minimum Essential Medium and 2 vol sodium bicarbonate (0.15 M) [R. F. Nicosa and A. Ottinetti, *Lab. Invest*, Vol. 63, pp. 115–122 (1990)].

Bovine aortic endothelial cells were seeded into 16 mm wells of a 24-well plate and allowed to grow for 24 h, to obtain a subconfluent monolayer. The culture medium was then removed and 0.4 ml of the cold collagen mixture described above were poured on top of the cell monolayer and allowed to polymerize for 10 min at 37° C. Fresh medium (0.6 ml), containing bFGF (1 ng/ml) and heparin (1 μg/ml), with (FIG. 3B) or without (FIG. 2A) 0.1 μg/ml of Halofuginone, was added after the collagen had gelled. The reorganization of the endothelial cell monolayer was monitored and photographed with a Zeiss inverted phase contrast photomicroscope [K. Monesano, et al., *J. Cell Biol.*, Vol. 97, pp. 1648–1652 (1983)].

Figure 3A:
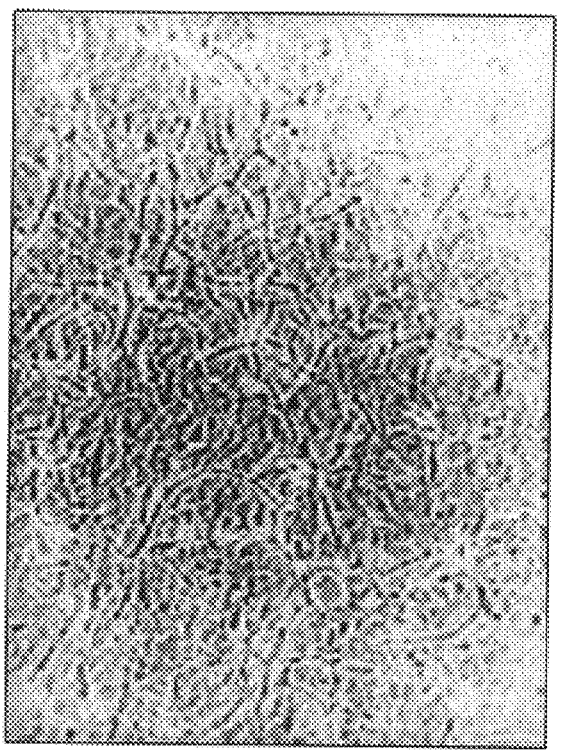
FIGS. 3A and 3B illustrate the inhibitory effect of Halofuginone on the organization of bovine aortic endothelial cells onto capillary-like networks.
Figure 3B:
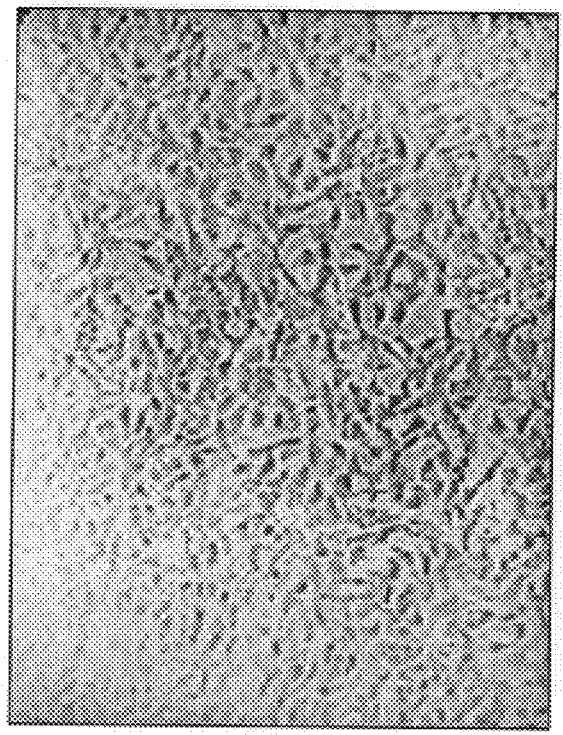

FIG. 3A illustrates the organization of endothelial cells into capillary-like networks. Such organization is inhibited by Halofuginone, as demonstrated by FIG. 3B. Halofuginone completely inhibited the invasion of the endothelial cells into the collagen gel and their subsequent organization into a network of branching and anastomosing capillary-like tubes.

EXAMPLE 4

Microvessel Formation

Halofuginone was shown to inhibit microvessel formation from rings of aortic tissues taken from rats. This effect was also shown to be reversible upon removal of Halofuginone. Results are shown in FIGS. 4A, 4B, 5 and 6.

Thoracic aortas were obtained from 1- to 2-month-old SD (Sprague-Dawley) rats sacrificed by decapitation [R. F. Nicosia and A. Ottinetti, *Lab. Invest*, Vol. 63, pp. 115–122 (1991)]. The aortas were immediately transferred to a Petri dish with PBS. The fibro-adipose tissue around the aorta was carefully removed under a dissecting microscope, and 1 mm-long aortic rings were sectioned and extensively rinsed in PBS.

Type I collagen solution (0.2 ml) was added to each 16-mm well and gellation was allowed for 15 min at 37° C. Each aorta ring was transferred and positioned to the center of the gel and another 0.4 ml of the collagen solution was carefully poured on top of the ring. After the gel was formed, 0.4 ml of serum free, endothelial growth medium, with or without 0.1 μg/ml Halofuginone, was added and the medium was changed every other day.

Figure 4A:
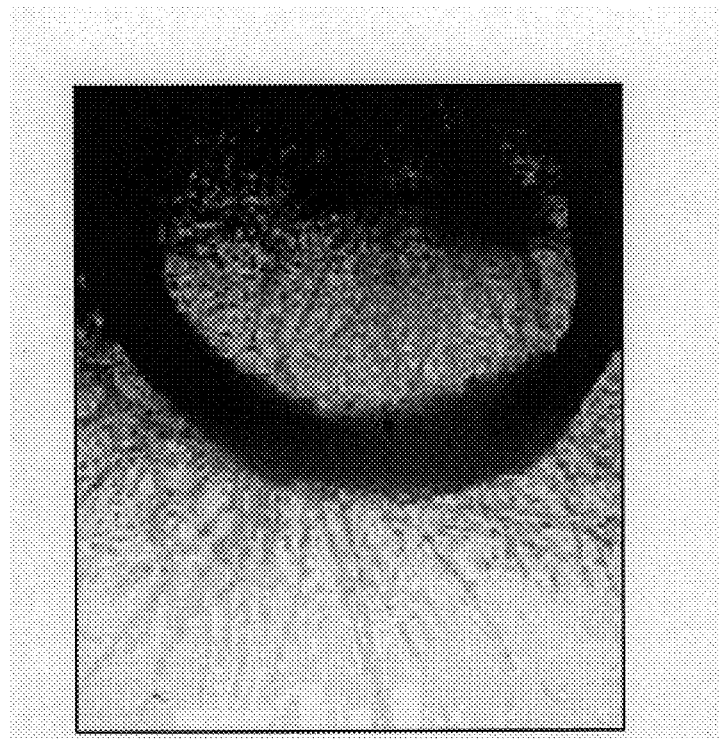
FIGS. 4A and 4B pictorially illustrate the inhibitory effect of Halofuginone on microvessel formation from rat aortic rings embedded in type I collagen gel.
Figure 4B:
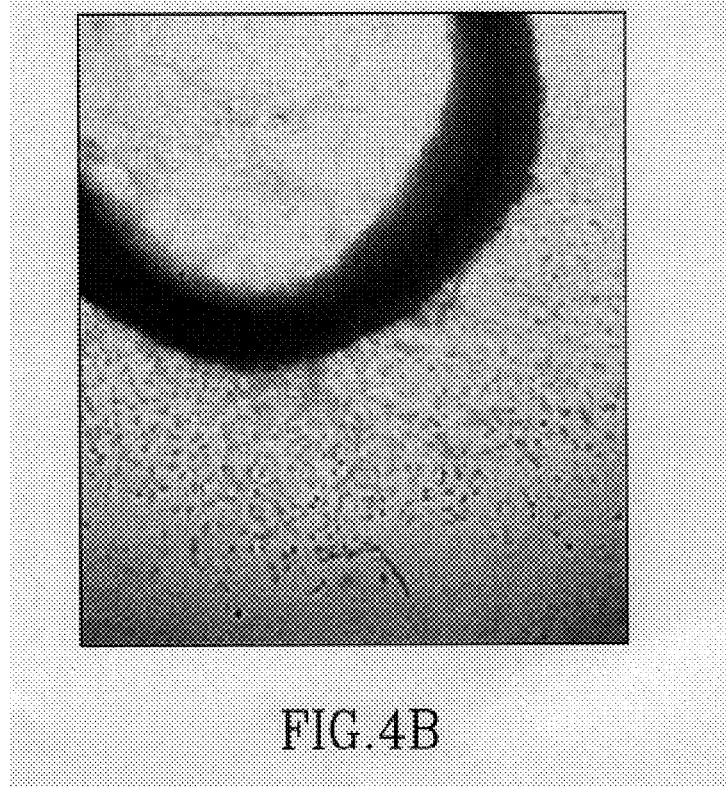

FIG. 4A shows the culture at day 10, when the newly-formed branching microvessels were developed from the end of reaction of the aorta, giving rise to loops and networks. FIG. 4B shows the same culture treated with 0.1 μg/ml halofuginone, replaced every other day. Under these conditions, single cells were migrating from the aortic ring toward the periphery, but failed to align into microvessel tubes.

Figure 5:
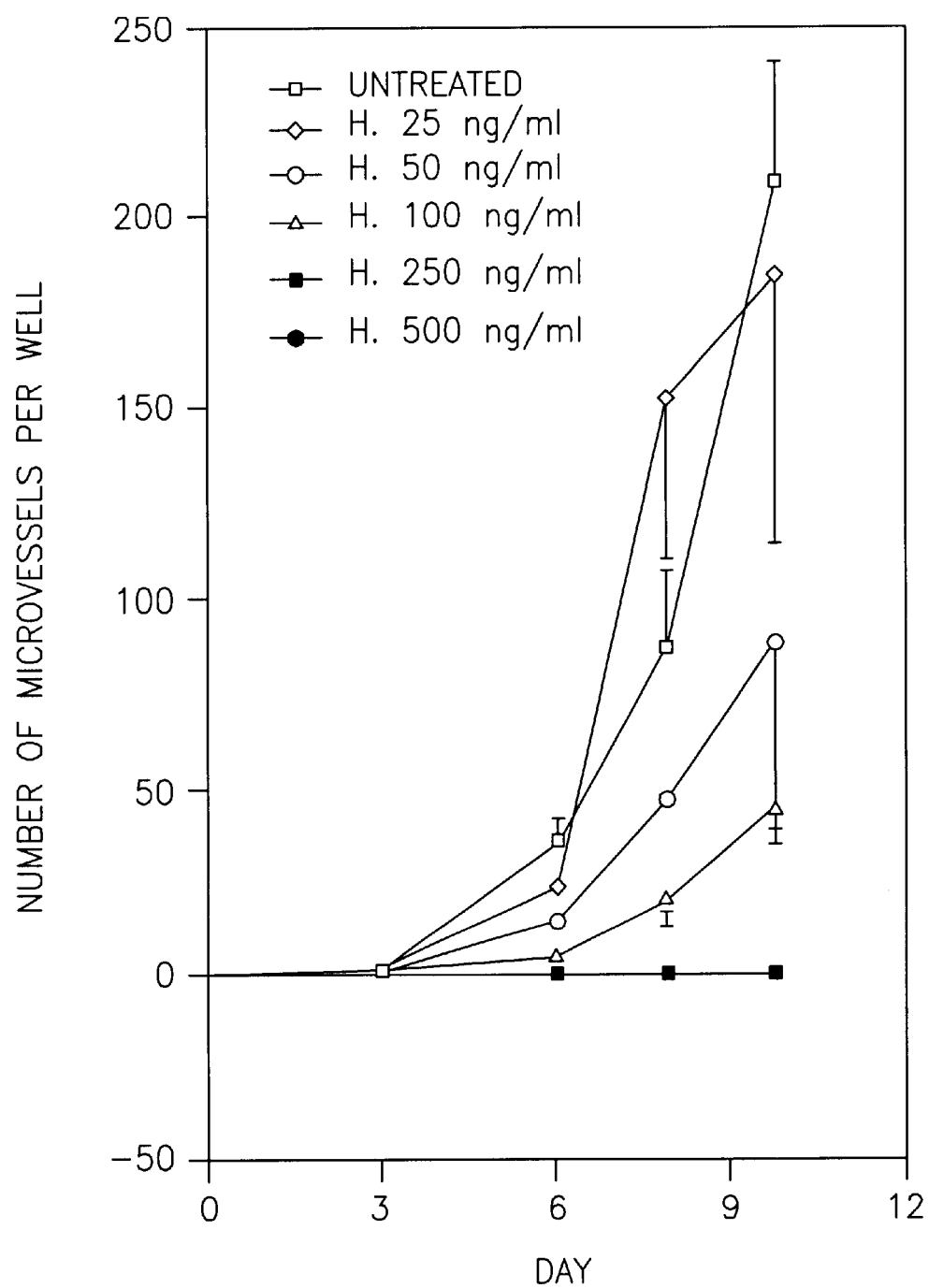
FIG. 5 is a dose-response curve of the inhibitory effect of Halofuginone on microvessel formation, using the collagen Type I embedded rat aortic rings of FIGS. 4A and 4B.
Figure 6:
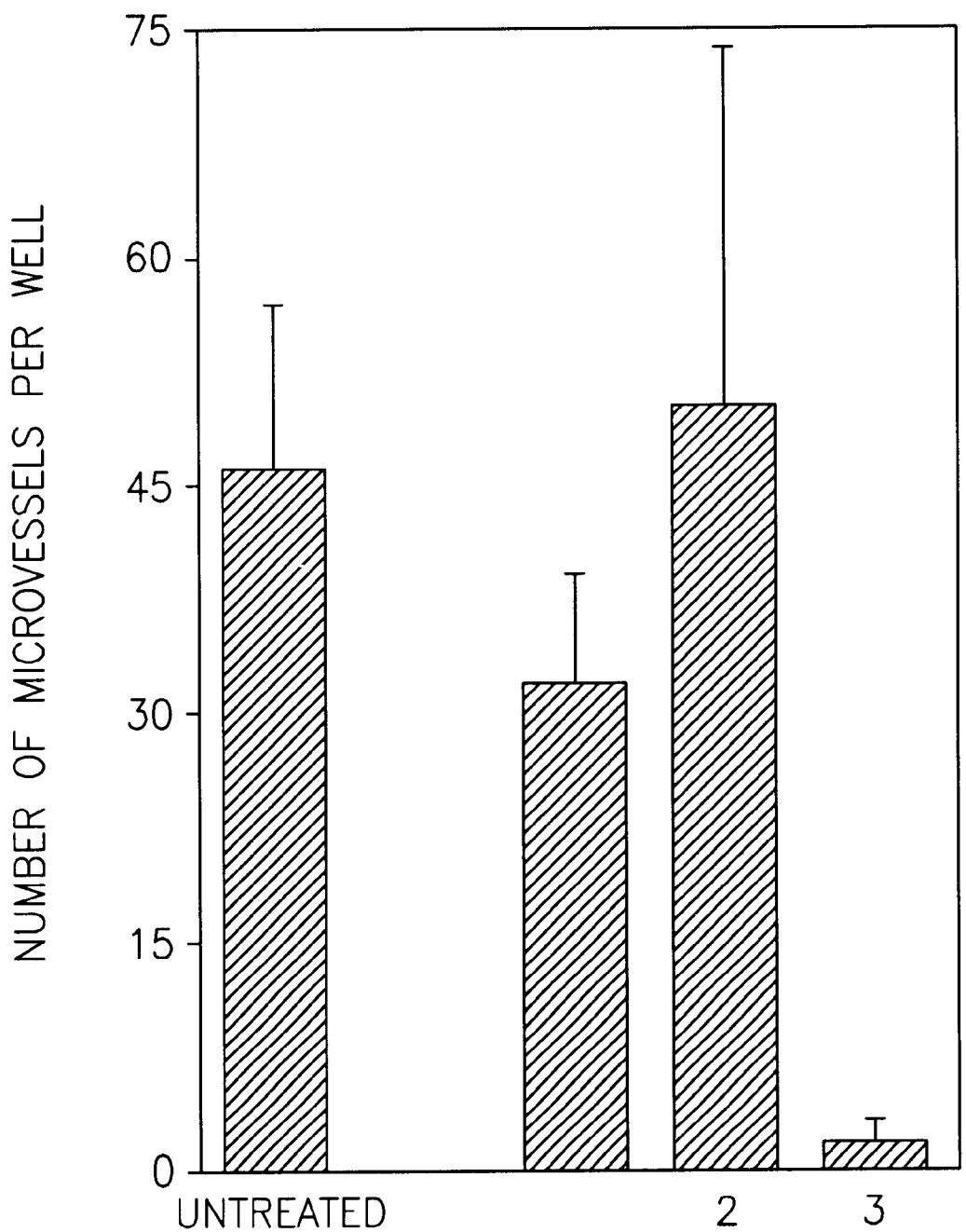
FIG. 6 demonstrates the reversibility of the inhibitory effect of Halofuginone.

FIG. 5 shows this effect quantitatively, at increasing doses of Halofuginone. An almost complete inhibition of microvessel formation was obtained at 100 ng/ml Halofuginone. Complete inhibition was observed as the presence of 250 ng/ml Halofuginone. This effect was reversed upon removal of the drug on day 2, as shown in FIG. 6. Such removal resulted in microvessel formation, similar to that seen with untreated aortic rings.

EXAMPLE 5

Figure 7:
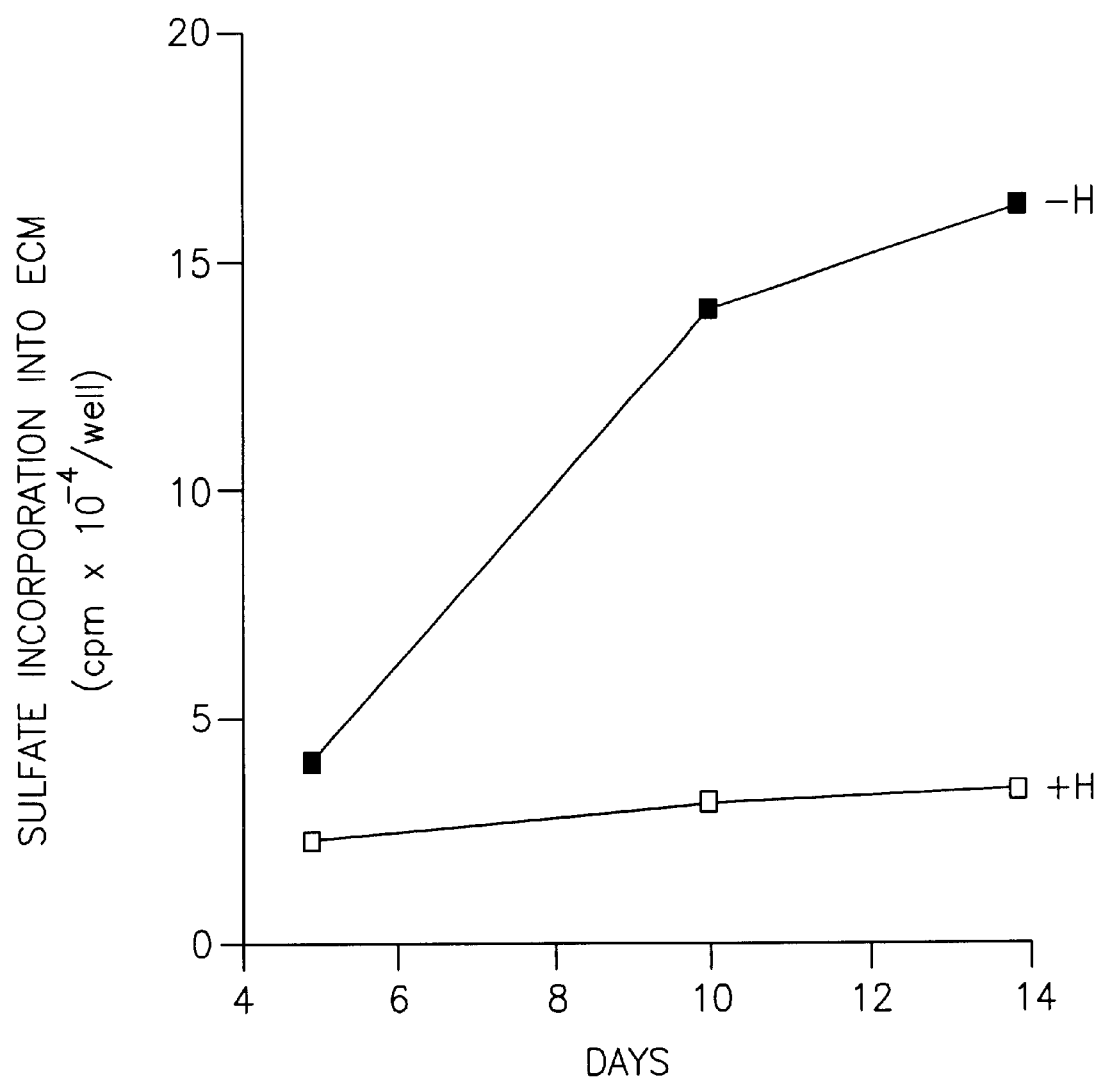
FIG. 7 shows the effect of Halofuginone on sulfate incorporation into the subendothelial ECM with bovine corneal endothelial cells.

Halofuginone inhibition of Sulfate Incorporation into FCM of Cultured Endothelial Cells Halofuginone was shown to have an inhibitory effect on the deposition of ECM (extracellular matrix components), as shown in FIG. 7 and in other examples below.

Cultures of bovine corneal endothelial cells were established from steer eyes and maintained as previously described [D. Gospodarowicz, et al., *Exp. Eye Res.*, No. 25, pp. 75–89 (1997)]. Cells were cultured at 37° C. in 10% $CO_2$ humidified incubators and the experiments were performed with early (3–8) cell passsages.

For preparation of the sulfate-labelled ECM (extracellular matrix), corneal endothelial cells were seeded into 4-well plates at a confluent density forming, within 4–6 h, a contact inhibited cell monolayer composed of closely apposed, and growth arrested cells. Under these conditions, the cells remained viable and retained their normal monolayer configuration and morphological appearance up to a concentration of 2 μg/ml halofuginone. $Na_2[^{35}S]O_4$ (540–590 mCi/mmol) was added (40 μCi/ml) one and five days after seeding and the cultures were incubated without medium change. At various intervals after seeding, the subendothelial ECM was exposed by dissolving (5 min., room temperature) the cell layer with PBS containing 0.5% Triton X-100 and 20 mM $NH_4OH$, followed by four washes in PBS [I Viodavsky, et al., *Cancer Res.*, Vol. 43, pp. 2704–2711 (1983), I. Vlodavsky, et al., *Proc. Natl. Acad. Sci. USA*, Vol. 84 pp. 2292–2296 (1987)]. To determine the total amount of sulfate labeled material, the BCM was digested with trypsin (25 μg/ml, 24 h, 37° C.) and the solubilized material counted in a β-counter.

FIG. 7 shows the almost complete inhibition of sulfate incorporation by 1 μg/ml Halofuginone, while 50% inhibition was obtained in the presence of 0.2 μg/ml of the drug.

EXAMPLE 6

Figure 8A:
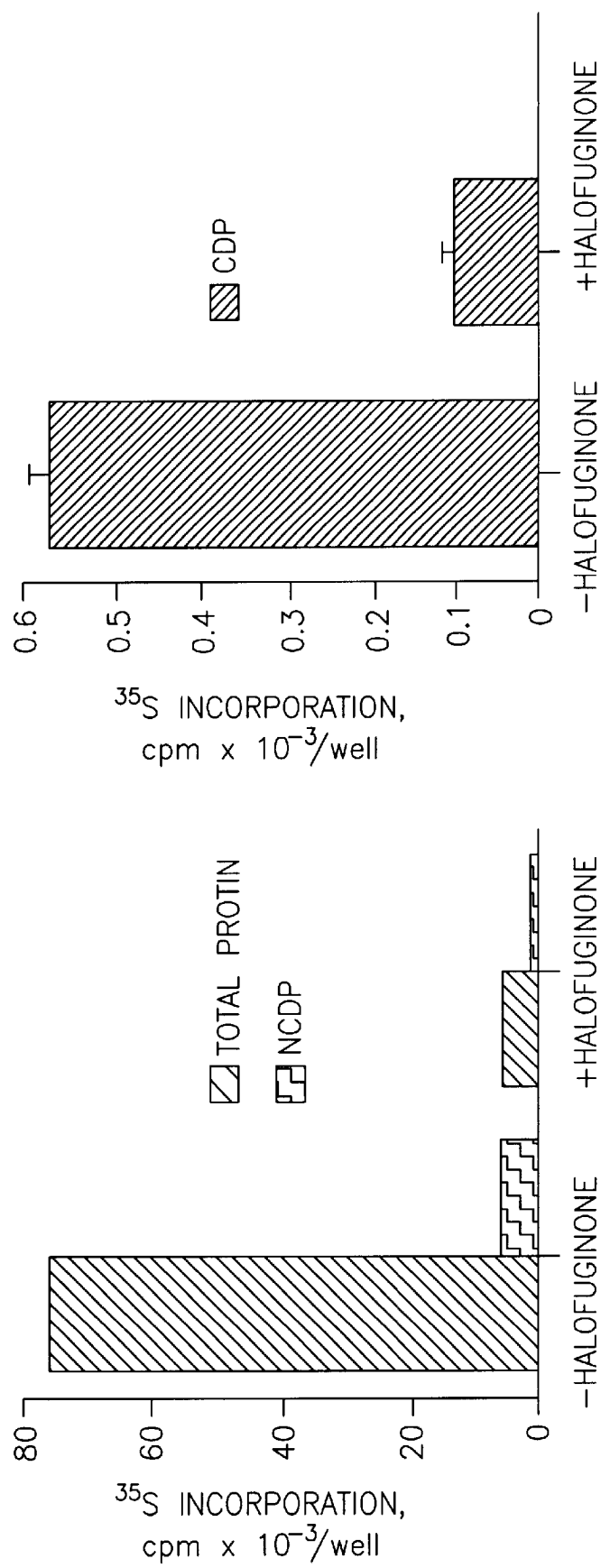
FIGS. 8A–8D compare the effect of Halofuginone on incorporation of sulfate, proline, lysine and glycine into the ECM by bovine corneal endothelial cells.
Figure 8B:
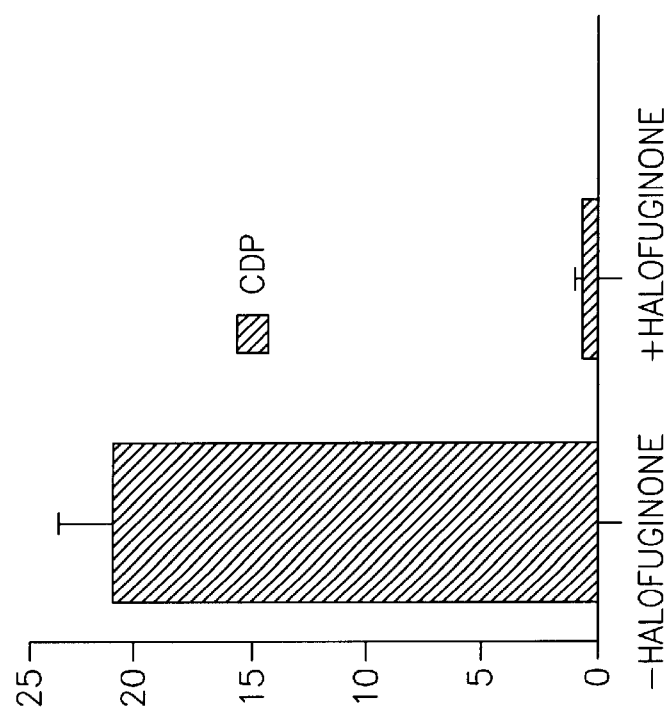
Figure 8B:
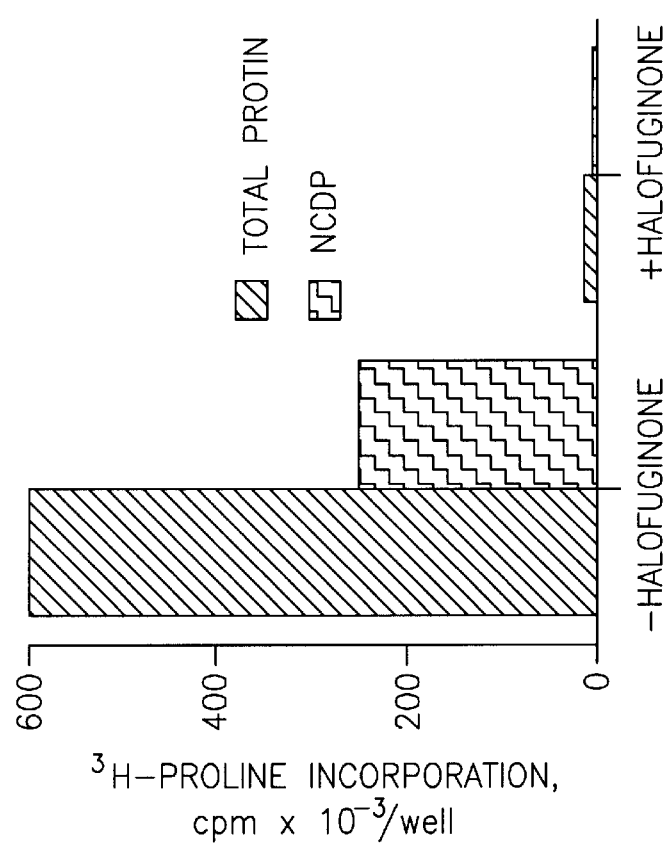
Figure 8C:
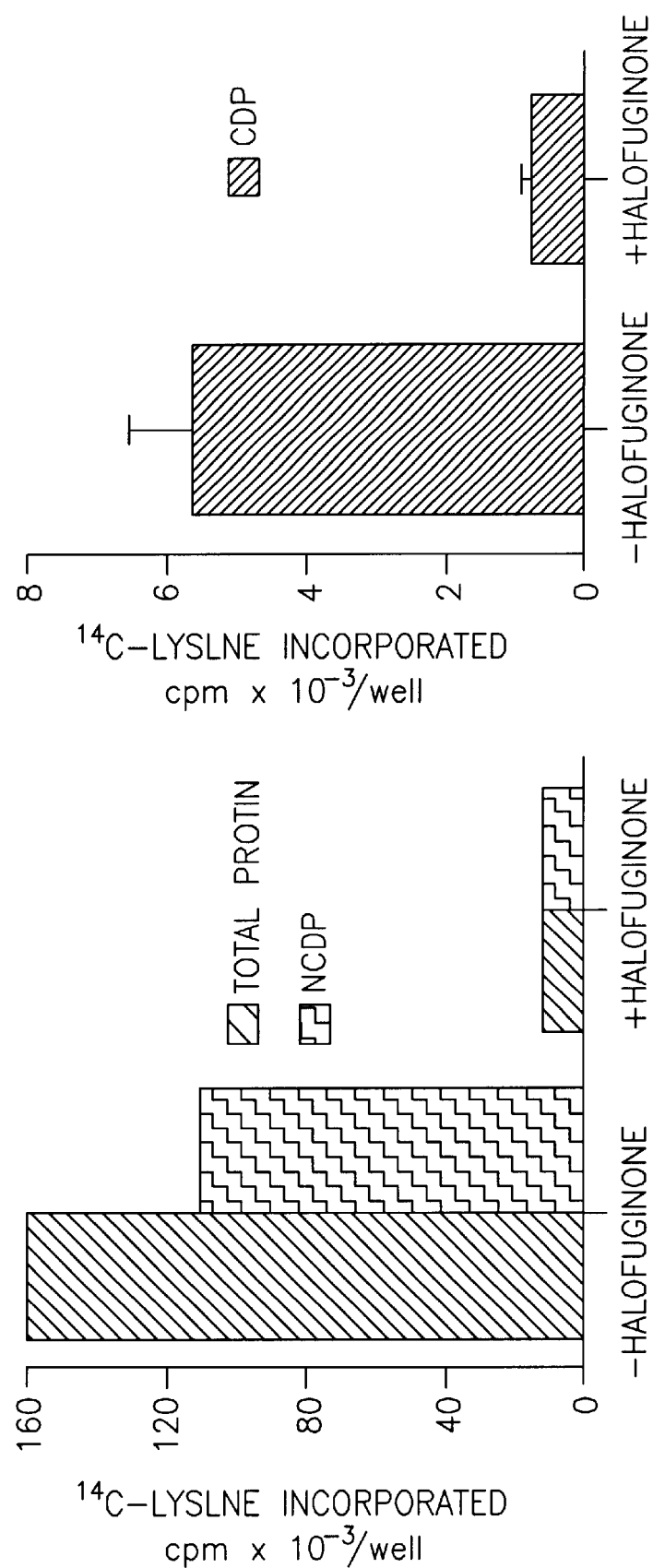
Figure 8D:
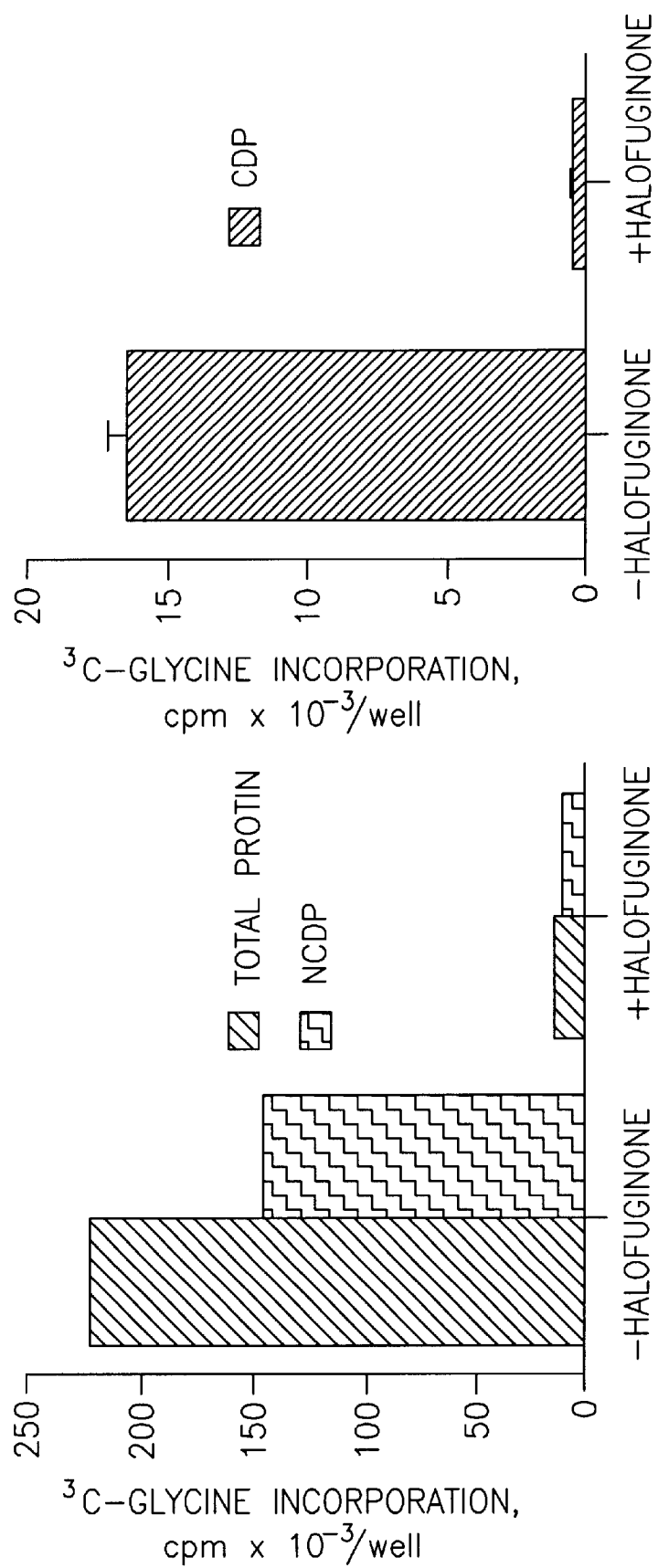

Inhibition of Incorporation of Sulfate Proline, Lysine and Glycine into ECM of Bovine Corneal Endothelial Cells Corneal endothelial cells were seeded at a confluent density and grown as described in Example 5 above. The cells were cultured with or without Halofuginone in the presence of either Na$_2^{35}$SO$_4$ (FIG. 8A), $^3$H-proline (FIG. 8B), $^{14}$C-lysine (FIG. 8C) or $^{14}$C-glycine (FIG. 8B). Eight days after seeding, the cell layer was dissolved substantially as described in Example 5 above. The underlying ECM was then either trypsinized to determine the effect of Halofuginone on incorporation of labelled material into total protein, substantially as described in Example 5 above, or subjected to sequential digestions with collagenase and trypsin to evaluate the effect of Halofuginone on both collagenase-digestible proteins (CDP) and non-collagenase digestible proteins (NCDP).

As FIGS. 8A–8D show, Halofuginone inhibited the incorporation of sulfate, proline, lysine and glycine into both CDP and NCDP, reflecting a profound inhibition of matrix deposition. The inhibitory effect of Halofuginone on deposition of ECM components other than collagen is most likely due to the involvement of collagen in the assembly of other constituents into the supramolecular structure of the ECM. Alternatively, Halofuginone may affect the synthesis of ECM components other than collagen, possibly through a common transcription factor or cytokine such as TGFβ, which affects the synthesis and deposition of several ECM components.

EXAMPLE 7

Figure 9B:
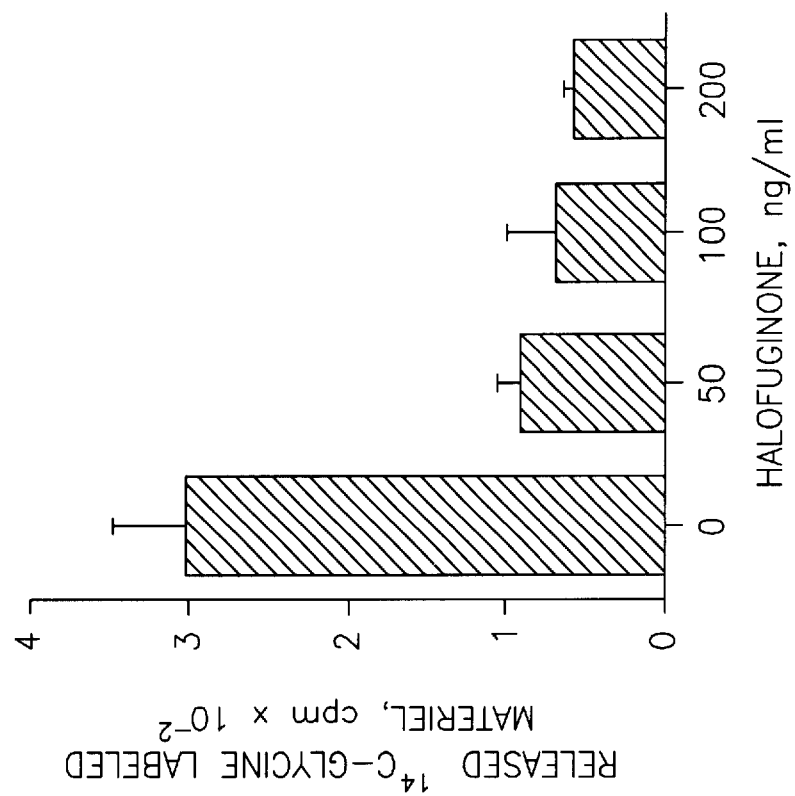
FIGS. 9A–9D illustrate the effect of Halofuginone on sulfate and glycine incorporation into the ECM of rat mesengial cells.
Figure 9A:
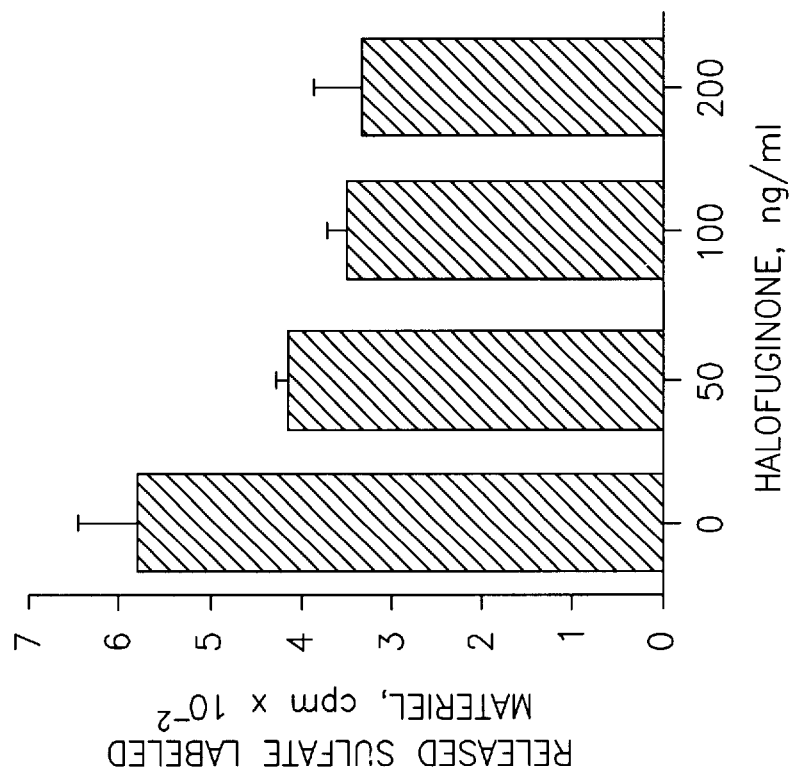
Figure 9D:
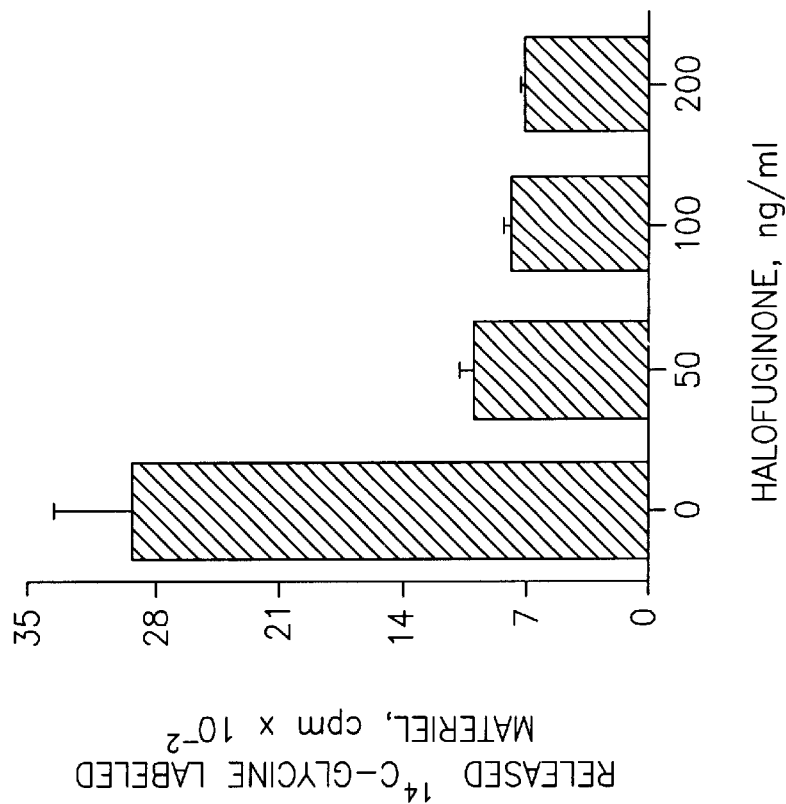
Figure 9C:
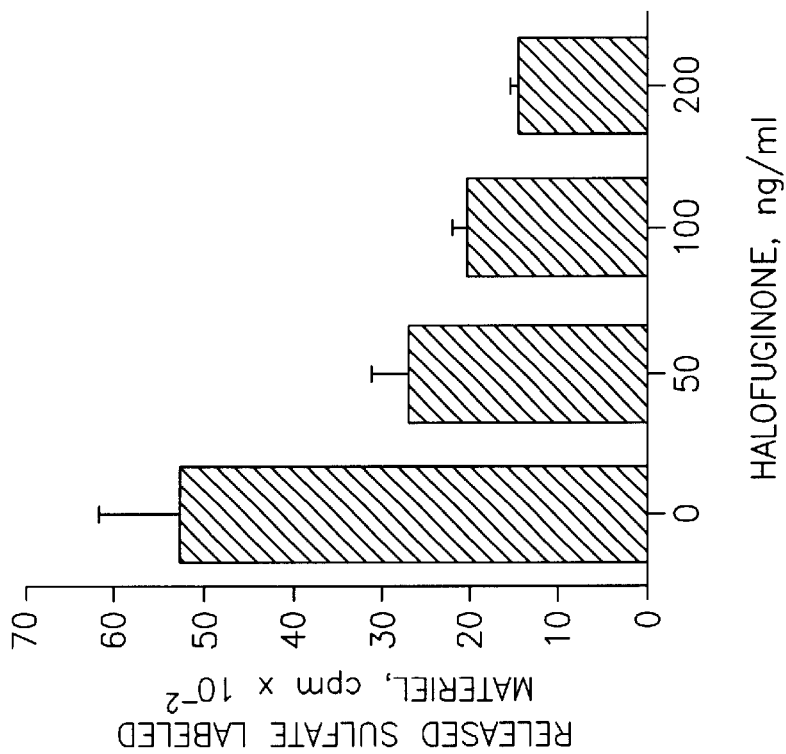

Inhibition of Sulfate and Glycine Incorporation into Rat Mesengial Cell ECM Rat mesengial cells were grown to confluency, 24 hours after seeding. The cells were then cultured with or without Halofuginone in the presence of either Na$_2^{35}$SO$_4$ (FIGS. 9A and 9B) or $^{14}$C-glycine (FIGS. 9C and 9D). Eight days after sending, the cell layer was dissolved to expose the underlying ECM, washed and digested with collagenase to determine the effect of Halofuginone on CDP proteins, as shown in FIGS. 9A and 9C. The remaining material was digested with trypsin and subjected to β-scintillation counting to determine the effect of halofuginone on NCDP proteins, as shown in FIGS. 9B and 9D.

About 30% inhibition of sulfate incorporation was seen for CDP proteins, while about 70% inhibition was seen for NCDP proteins in the presence of 200 ng/ml Halofuginone. It should be noted that the inhibition of ECM deposition by Halofuginone was not due to its anti-proliferative activity since the drug was added to highly confluent, non-dividing cells. Since inorganic sulfate as incorporated primarily into sulfated glycosaminoglycans and not into collagen, it is conceivable that by inhibiting type I collagen, synthesis, Halofuginone interferes with the assembly of other ECM macromolecules, such as heparin sulfate proteoglycans, which are known to specifically interact with collagen to from ECM.

About 80% inhibition of glycine incorporation was seen for both CDP and NCDP proteins in the presence of 50 ng/ml Halofuginone. The inhibitory effect of Halofuginone on deposition of collagenase-digestible ECM proteins was more pronounced with glycine than with sulfate labeled matrix since unlike glycine, sulfate is incorporated primarily into glycosaminoglycans which are not degraded by collagenase. A profound inhibition of ECM deposition was supported by a microscopic examination of the denuded culture dishes, revealing a thin or non-existant layer of ECM produced in the presence of Halofuginone.

EXAMPLE 8

Inhibitory Effect of Halofuginone on In Vivo Neovascularization

Halofuginone was shown to inhibit angiogenesis in an in vivo model. Such an inhibitory effect also demonstrates the ability of Halofuginone to inhibit cell proliferation which is enabled by the deposition of ECM components. Results are given in FIGS. 10A and 10B, and in Table 3 below.

A murine corneal angiogenesis model was used to evaluate the inhibitory effect of Halofuginone in vivo. The angiogenic factor bFGF was applied into a corneal pocket in a pellet made of a slow release polymer, as described below, and Halofuginone (2 μg/mouse/day) was administered i.p. for 5 consecutive days.

The pellets were made of the slow-release polymer Hydron (polyhydroxyethylmethacrylate [polyHEMA], Interferon Sciences, N.J.) containing sucralfate alone, or sucralfate and bGFG. A suspension of sterile saline 10 μg recombinant bFGF plus 10 mg of sucralfate was prepared and speed vacuumed for 5 minutes. To this suspension, 10 μl of 12% Hydron in ethanol was added. The suspension was then deposited onto an autoclave sterilized, 15×15 mm piece of nylon mesh (TETKO, 3-300/50, approximate pore size 0.4×0.4 mm) and embedded between the fibers resulting in a grid of 10×10 squares. Both sides of the mesh were then covered with a thin layer of Hydron to hydrophobically stabilize the pellet during implantation. These layers were allowed to dry on a sterile petri dish for 30 minutes. Subsequently, the fibers of the mesh were pulled apart under a microscope, and about 30–40 uniformly sized pellets of 0.4×0.2×0.2 mm, containing approximately 80–100 ng bGFG per pellet, were collected. Such pellets can be stored frozen at −20° C. for several weeks without loss of bioactivity.

C57B⅙ mice of about 7–9 weeks of age were anesthetized with methoxyflurane. The eyes were topically anesthetized with 0.5% proparacaine, and the globe was proposed with a jeweler's forceps. A central, intrastromal linear keratotomy of approximately 0.6 mm length was performed with a surgical blade and a lamellar micropocket was dissected towards the temporal limbus. The temporal extent of the packet was within 0.7–1.0 mm of the limbus. A single pellet was then placed on the corneal surface at the base of the pocket with jeweler's forceps, and using one arm of the forceps, the pellet was advanced toward the temporal end of the pocket. Antibiotic ointment (erythromycin) was applied once to the operated eye, not only to prevent infection, but also to decrease irritation of the irregular ocular surface. The eyes routinely examined by sin-lamp biomicroscopy on post-operative days 3 through 5 following pellet implantation.

On post-operative day 5, mice were anesthetized with methoxyflurane, the eyes were proptosed, and the maximum vessel length (VL) of the neovascularization zone extending from the base of the limbal vascular plexus toward the pellet was measured with a linear reticule through the slit lamp. The contiguous circumferential zone of neovascularization (CH) was measured as clock hours with a 360 degree reticule. The eyes were photographed on day 5 and the slides were used to determine the area of neovascularization, in square men.

The area of neovascularization was calculated according to the following formula:

$$A = \frac{(CH*0.8)*0.5*VL*\pi}{2}$$

where A is area, CH is contiguous circumferential zone of neovascularization and VL is maximal vessel length.

Figure 10A:
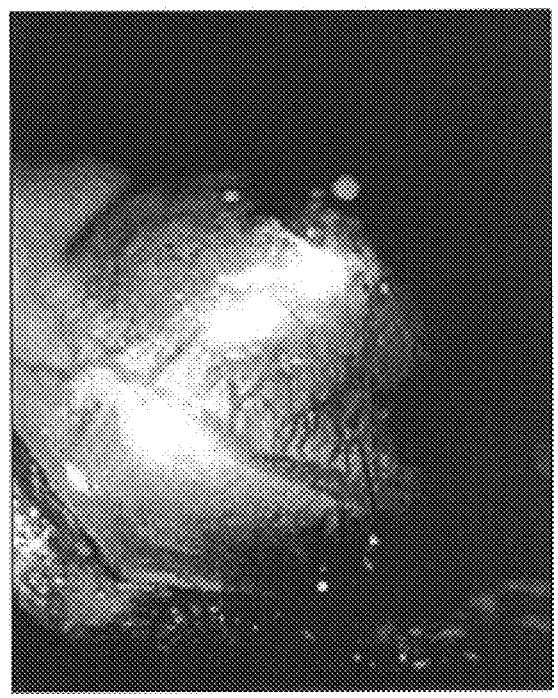
FIGS. 10A and 10B illustrate the inhibitory effect of Halofuginone on in vivo neovascularization in the eyes of mice.
Figure 10B:
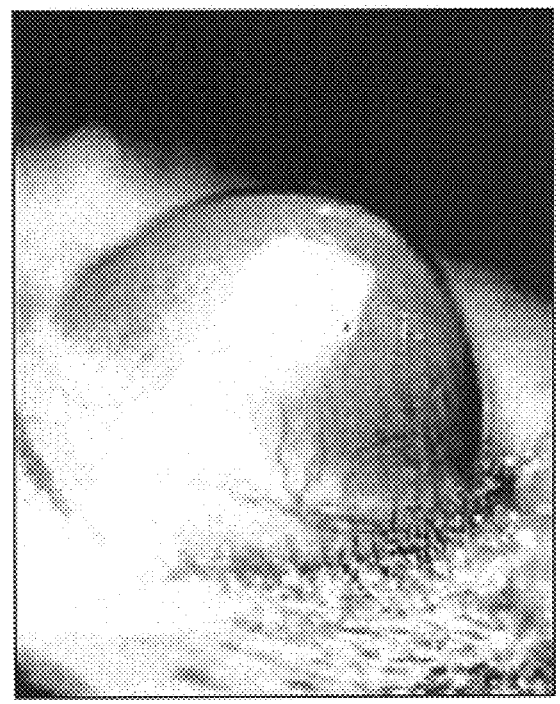

FIG. 10A demonstrates that control group was 2.66 mm$^2$ (n=8). FIG. 10B shows that neovascularization was inhibited by Halofuginone, as the average area of neovascularization was 1.90 mm² (n=7), for an inhibition of about 29%. Data for all mice are shown in Table 3 below.

TABLE 3

Inhibition of Angiogenesis by Halofuginone

| Sample No. | VL for Control | VL for Halofuginone | CH for Control | CH for Halofuginone |
|---|---|---|---|---|
| 1 | 1.2 | 0.9 | 4 | 3 |
| 2 | 1.2 | 1 | 4 | 2.5 |
| 3 | 1.2 | 1.2 | 5 | 4 |
| 4 | 1.1 | 1 | 3 | 1 |
| 5 | 1.2 | 1 | 3 | 3.5 |
| 6 | 1 | 1.1 | 4 | 3 |
| 7 | 1.1 | 1.2 | 3 | 3 |
| 8 | 1 | NA | 4 | NA |

EXAMPLE 9

Effect of Halofuginone on Proliferation of Human Leiomyosarcoma Tumor Cells

The effect of Halofuginone on proliferation of human leiomyosarcoma tumor cells was investigated Leiomyosarcoma tumors have abundant extracellular matrix and are also well vascularized [A. Ferenczy, et al., Cancer, No. 28, pp. 1004–1018 (1971)]. Their growth is thought to be dependent on growth factors (i.e., bGFG, HB-FGF) produced by normal and malignant myometrial cells [A. Zhang, et al., Endocrinology, No. 134, pp. 1089–1094 (1994); R. S. Mangrulker, et al., Biology of Reproduction No. 53, pp. 636–646 (1995)] and locally embedded in the surrounding ECM [I. Viodavsky, et al., Basement Membranes: Cellular and Molecular Aspects, D. E. Rohrbach and R. Timp., Eds. Academic Press, Inc., Orlando, Fla. U.S.A., pp. 327–343 (1993)].

Samples of human leiomyosarcoma tumors were obtained from women undergoing surgical hysterectomy, as described [R. S. Mangrulker, et al., ibid.]. Minced tissue was placed into 20 ml cold homogenization buffer: 1 M NaCl, 10 mM Tris (pH 7.4), 1 mM EDTA, 1 mM benzamidine, 0.1% CHAPS, 0.01% Aprotinin (Sigma), 10 μg/ml leupeptin, 1 mM AEBSF [R. S. Mangrulker, et al., ibid]. Samples were homogenized for 2 min and centrifuged at 12000 a g for 60 min at 4° C. The supernatants were diluted 1:5 with 10 mM Tris (pH 7.4) to a final volume of 100 ml and filtered with 0.45 μm nylon fibers. Cells were plated and maintained in DMEM plus 10% calf serum. The cells remained viable over a number of passages but were used at passages 2 or 3.

For proliferation assays, cells were plated in 96-well plates at 10,000 cells/well an 200 μl medium (DMEM with 4.5 G/L glucose, 10% calf serum. 1% glutamine, 1% penicillin/streptomycin) and incubated 2 days until confluent. 24 h after seeding, increasing concentrations of Halofuginone (10–100 mg/ml) were added. The medium was changed to DMEM with 0.5%calf serum, 1 μM insulin and 5 μM transferrin. After 24 h, the samples (5–10 μl) were added and after an additional 24 h, [³H]thymidine (1 μCi/well) was added to each well. After 36–48 h incubation, the cells were fixed with methanol, and the DNA was precipitated with 5% trichloroacetic acid. The cells were lysed with 150 μl/well of 0.3 N NaOH, transferred to scintillation vials, and counted on a β-counter. As demonstrated in FIG. 11A, 60–70% inhibition of [³H]thymidine incorporation was obtained at 2.5 ng/ml Halofuginone.

Figure 11A:
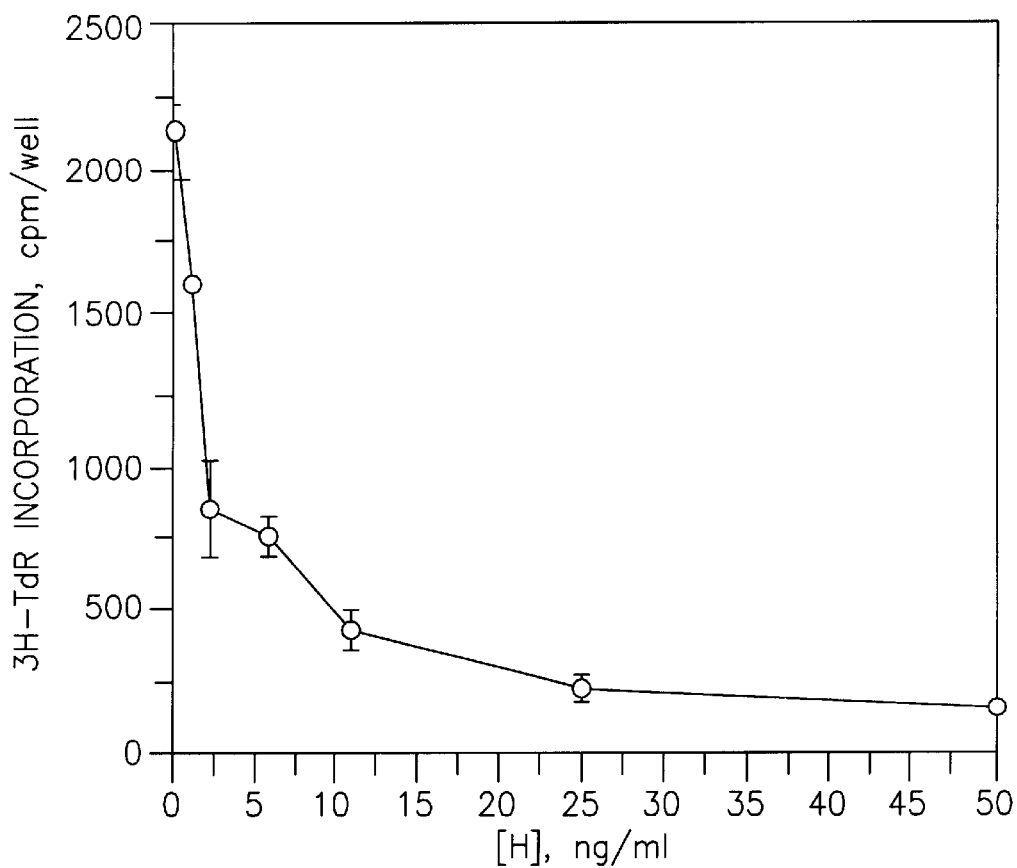
FIGS. 11A and 11B illustrate the effect of Halofuginone on ³H-thymidine incorporation and proliferation of human leiomyosarcoma tumor cells.
Figure 11B:
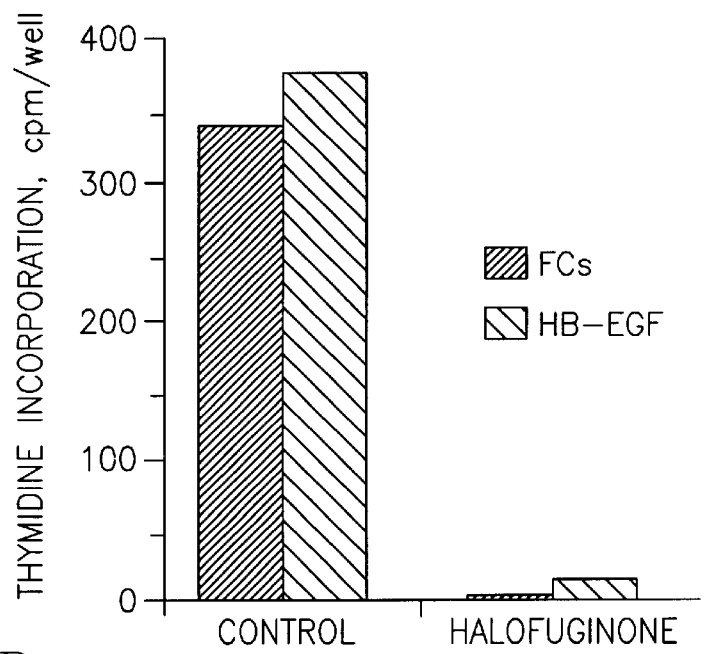

The effect of Halofuginone on proliferation of HB-EGF (Heparin-Binding Epidermal Growth Factor) and serum-stimulated leiomyosarcoma cells was then examined. The leiomyosarcoma tumor cells were growth-arrested by 48 h incubation in medium containing 0.5% FCS. The cells were then exposed (24 h) to either 10% FCS or 10 ng/ml HB-EGF in the absence or presence of 10 ng/ml Halofuginone. [³H]thymidine was then added and DNA synthesis measured 36 h later. A complete inhibition of cell proliferation induced by both serum or HB-EGF was observed in the presence of Halofuginone, as shown in FIG. 11B.

EXAMPLE 10

Inhibition of Collagen Type I Gene Expression by Halofuginone

Figure 12:
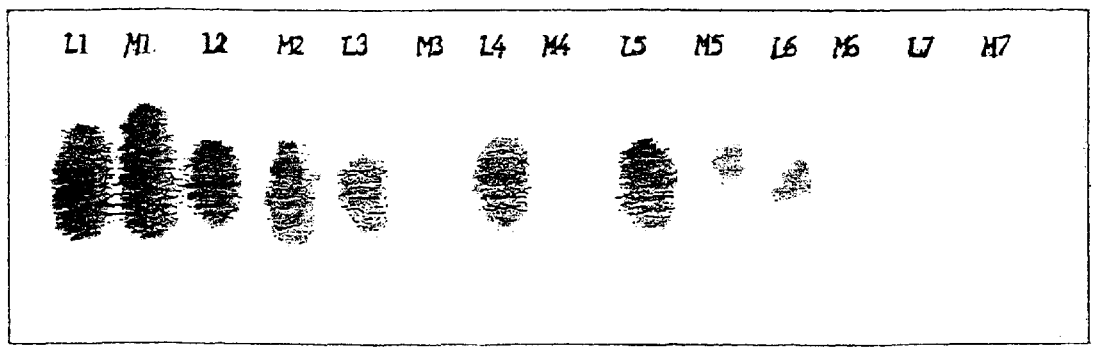
FIG. 12 illustrates the inhibition of collagen I gene expression by Halofuginone.

Myometrial and leiomyosarcoma cells were taken from the same patient and were plated into 10 cm plates in DMEM supplemented with 10% FCS. When the cells reached 80% confluence, the medium was replaced by serum free DMEM plus 0.1% BSA for 48 hours, washed and exposed to increasing concentrations of Halofuginone in the same medium for about 48 hours at about 37° C. The cells were then harvested and subjected to RNA extraction and Northern blot analysis for collagen type I gene expression. As demonstrated in FIG. 12, Halofuginone inhibited collagen type I gene expression (products at 5.4 and 4.8 kb) in a dose-dependent manner. Furthermore, the effect on myometrial cells (lane M4, 50 ng/ml) as compared to leiomyosarcoma (lane L6, 200 ng/ml) cells.

EXAMPLE 11

Suitable Formulations for Administration of Halofuginone

Halofuginone can be administered to a subject in a number of ways, which are well known in the art. Hereinafter, the term "subject" refers to the human or lower animal to whom Halofuginone was administered. For example, administration may be done topically (including ophtalmically, vaginally, rectally, intranasally), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical cameras, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the subject to Halofuginone. Persons of ordinary skill in the art can easily determine optimum dosages, dosing methodologies and repetition rates.

EXAMPLE 12

Method of Treatment of Malignancies

As noted above, Halofuginone has been shown to be an effective inhibitor of tumor progression by inhibiting angiogenesis. The following example is an illustration only of a method of treating malignancies with Halofuginone, and is not intended to be limiting.

the method includes the step of administering Halofuginone, in a pharmaceutically acceptable carrier as described in Example 12 above, to a subject to be treated. Halofuginone is administered according to an effective dosing methodology, preferably until a predetermined endpoint is reached, such as the absence of a particular tumor marker in a sample taken from the subject.

Examples of tumors for which such a treatment would be effective include, but are not limited to, breast cancers such as infiltrating duct carcinoma of the breast, lung cancers such as small cell lung carcinoma, bone cancers, bladder cancers such as bladder carcinoma, rhabdomyosarcoma, angiosarcoma, adenocarcinoma of the colon, prostate or pancreas, squamous cell carcinoma of the cervix, ovarian cancer, malignant fibrous histiocytoma, skin cancers such as malignant melanoma, leiomyosarcoma, astrocytoma, glioma and heptocellular carcinoma.

EXAMPLE 13

Method of Manufacture of a Medicament Containing Halofuginone

The following is an example of a method of manufacturing Halofuginone. First, halofuginone is synthesized in accordance with good pharmaceutical, manufacturing practice. Examples of methods of synthesizing Halofuginone, and related quinazolinone derivatives, are given in U.S. Pat. No. 3,338,909. Next, Halofuginone is placed in a suitable pharmaceutical carrier, as described in Example 11 above, again in accordance with good pharmaceutical manufacturing practice.

While the invention has been described with respect to a limited number of embodiments, it will be appreciated that many variations, modifications and other applications of the invention may be made.

What is claimed is:

1. A method for the inhibition of angiogenesis in a subject in seed thereof comprising the step of administering a pharmaceutically effective amount of a compound having a formula:

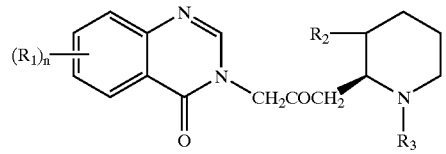

wherein:

n=1 or 2;

$R_1$ is a member of the group consisting of hydrogen, halogen, nitro, benzo, lower alkyl, phenyl, and lower alkoxy;

$R_2$ is a member of the group consisting of hydroxy, acetoxy and lower alkoxy; and $R^3$ is a member of the group consisting of hydrogen and lower alkenoxy-carbonyl.

2. The method according to claim 1, wherein said compound is halofuginone.

3. A method for the inhibition of angiogenesis according to claim 1 comprising a pharmaceutically-effective amount of a compound in a pharmaceutically-acceptable carrier.

* * * * *